(12) United States Patent
Deguchi et al.

(10) Patent No.: US 12,169,174 B2
(45) Date of Patent: Dec. 17, 2024

(54) GAS ANALYZER APPARATUS AND GAS ANALYSIS METHOD ANALIZING MEASUREMENT TARGET GAS USING LASER LIGHT

(71) Applicant: SMART LASER & PLASMA SYSTEMS CO., Tokushima (JP)

(72) Inventors: Yoshihiro Deguchi, Tokushima (JP); Takahiro Kamimoto, Tokushima (JP)

(73) Assignee: SMART LASER & PLASMA SYSTEMS CO., Tokushima (JP)

( * ) Notice: Subject to any disclaimer, the term of this patent is extended or adjusted under 35 U.S.C. 154(b) by 266 days.

(21) Appl. No.: 17/995,649

(22) PCT Filed: Apr. 1, 2021

(86) PCT No.: PCT/JP2021/014196
§ 371 (c)(1),
(2) Date: Oct. 6, 2022

(87) PCT Pub. No.: WO2021/205988
PCT Pub. Date: Oct. 14, 2021

(65) Prior Publication Data
US 2023/0160819 A1 May 25, 2023

(30) Foreign Application Priority Data
Apr. 10, 2020 (JP) ................................ 2020-070788

(51) Int. Cl.
*G01N 21/39* (2006.01)
*G01N 33/00* (2006.01)

(52) U.S. Cl.
CPC ......... *G01N 21/39* (2013.01); *G01N 33/0027* (2013.01); *G01N 2201/06113* (2013.01)

(58) Field of Classification Search
CPC ............... G01N 21/39; G01N 33/0027; G01N 2201/06113
See application file for complete search history.

(56) References Cited

U.S. PATENT DOCUMENTS 3,973,852 A * 8/1976 Moore ................. G01N 21/538
356/438
5,374,991 A * 12/1994 Atkinson ........... G01B 9/02081
356/493

(Continued)

FOREIGN PATENT DOCUMENTS

CN 1318760 A * 10/2001 ............... G02B 6/42
CN 108181269 A 6/2018

(Continued)

OTHER PUBLICATIONS

[English Translation] International Preliminary Report on Patentability mailed on Oct. 13, 2022 for International Patent Application No. PCT/JP2021/014196, pp. all.

(Continued)

*Primary Examiner* — Edmond C Lau
*Assistant Examiner* — Jarreas Underwood
(74) *Attorney, Agent, or Firm* — Dorsey & Whitney LLP

(57) ABSTRACT

This gas analysis device comprises: a laser light source which irradiates a gas to be measured with laser light; a laser control means which controls the laser light source so that the wavelength of the laser light is changed in each prescribed wavelength band; a light detection means which photoelectrically converts the laser light that have passed through the gas to be measured and outputs an electrical signal; and an interpretation means which analyzes, on the basis of the electrical signal, an absorption wavelength of the gas to be measured. In the gas analysis device, the laser control means controls the laser light source so that the intensity of the laser light changes into a shape (for example, (Continued)

a rectangular shape or a trapezoidal shape) having at least a substantially constant flat part in a prescribed time period, and the wavelength of the laser light changes in the time period.

16 Claims, 19 Drawing Sheets

(56) References Cited

U.S. PATENT DOCUMENTS

| | | |
|---|---|---|
| 2003/0160173 A1 | 8/2003 | Ershov et al. |
| 2009/0323068 A1 | 12/2009 | Yamakage et al. |
| 2016/0178517 A1 | 6/2016 | Deguchi et al. |
| 2022/0263292 A1* | 8/2022 | Kurita .................. H01S 5/4087 |

FOREIGN PATENT DOCUMENTS

| | | | |
|---|---|---|---|
| CN | 207730661 U | * | 8/2018 |
| JP | 2001066250 A | | 3/2001 |
| JP | 2008051598 A | | 3/2008 |
| JP | 2009222526 A | | 10/2009 |
| JP | 2011158426 A | | 8/2011 |
| JP | 2015040747 A | | 3/2015 |
| WO | 2021205988 A1 | | 10/2021 |

OTHER PUBLICATIONS

[English Translation] International Search Report mailed on Jun. 22, 2021 for International Patent Application No. PCT/JP2021/014196, pp all.

Lackner, Maximilian , "Tunable diode laser absorption spectroscopy (TDLAS) in the process industries—a review", Reviews in Chemical Engineering, vol. 23, Issue 2, Apr. 2007.

Murata, Akihiro , "Introduction of laser gas analyzer for process", Kangikyo, Japan Environmental Technology Association, Jan. 2010, pp. 18-19.

* cited by examiner

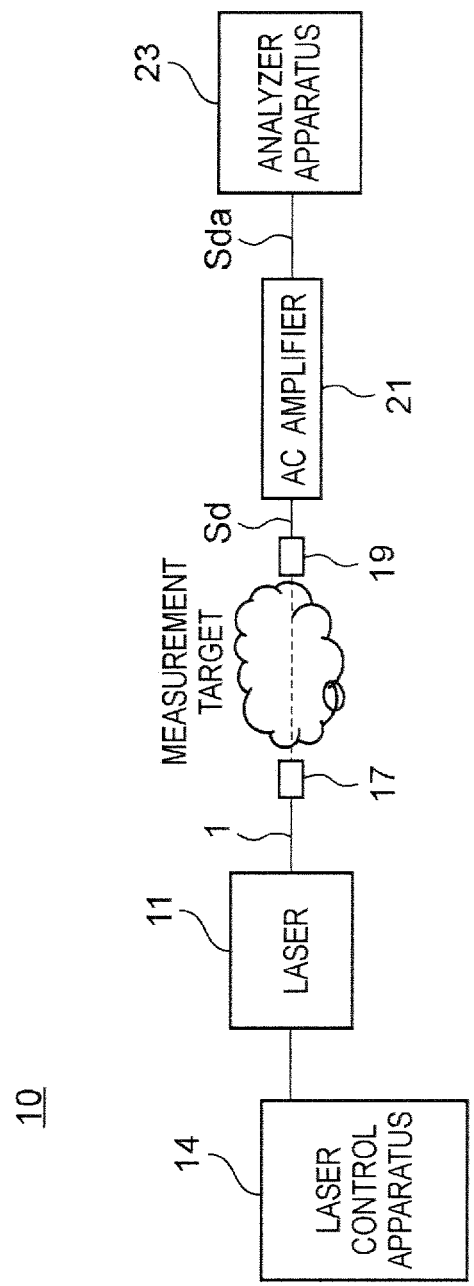

GAS ANALYZER APPARATUS AND GAS ANALYSIS METHOD ANALIZING MEASUREMENT TARGET GAS USING LASER LIGHT

CROSS REFERENCE TO RELATED APPLICATION(S)

This application is a U.S. National Stage filing under 35 U.S.C. § 371 of PCT Application No. PCT/JP2021/014196, filed Apr. 1, 2021, which claims priority to Japanese Application No. 2020-070788, filed Apr. 10, 2020, which are incorporated herein by reference, in their entirety, for any purpose.

TECHNICAL FIELD

The present invention relates to a gas analyzer apparatus and a gas analysis method for analyzing target gas using laser light.

BACKGROUND ART

In recent years, from the viewpoint of prevention of global warming, depletion of fossil fuels, environmental pollution, and the like, attention has been focused on global environmental conservation and effective use of energy in various fields, and for this reason, various environmental technologies have been studied.

In such an environmental technology, it is important to elucidate in detail a combustion structure of a combustion phenomenon in an engine, a burner, and the like and a transient behavior thereof. In recent years, a measurement technology utilizing a semiconductor laser absorption method has been developed as means for measuring temperature and concentration distribution in combustion gas in a time-series manner with high response.

In general, the absorption method is a measurement method utilizing the property of gas molecules to absorb infrared rays having wavelengths unique to chemical species and the temperature dependence and concentration dependence of the absorption amount. The concentration and temperature of the target gas can be measured by obtaining the ratio ($I_\lambda/I_{\lambda,0}$) of the intensity ($I_\lambda$) of the transmitted light to the intensity ($I_{\lambda,0}$) of the incident light when the incident light passes through the absorption medium (target gas) having a uniform optical path length (see, for example, Non-Patent Documents 1 and 2). In particular, the method of analyzing target gas using a phenomenon in which laser light having a predetermined wavelength is absorbed using a variable wavelength semiconductor laser is called tunable diode laser absorption spectroscopy (TDLAS).

The technologies for detecting a property (concentration or temperature) of measurement target gas by utilizing the absorption method using a semiconductor laser are disclosed in Patent Document 1 to 3 and the like.

For example, Patent Document 1 discloses a method in which laser light is demultiplexed into measurement laser light and reference laser light by a demultiplexer, the measurement laser light is transmitted into a gas and received by a photodetector, and an absorption spectrum absorbed by a gas component in the gas is grasped from light intensity of the received measurement laser light and light intensity of the reference laser light.

In addition, Patent Document 2 discloses a method in which, when an oscillation wavelength of laser light is modulated with a modulation signal of a predetermined frequency, there are provided a first time interval in which an absorption wavelength unique to a gaseous substance to be measured is modulated at a predetermined frequency and a second time interval in which a wavelength deviating from the unique absorption wavelength is modulated at a predetermined frequency, and an accurate gas concentration is obtained by subtracting an offset signal measured in the second time interval from a gas concentration signal including an offset signal measured in the first time interval.

Further, in Patent Document 3, the gas analyzer apparatus includes first and second laser light sources configured to output first laser light and second laser light, laser controller configured to control the first and second laser light sources such that wavelengths of the first laser light and the second laser light change in a predetermined wavelength band, a multiplexer configured to mix the first laser light and the second laser light and irradiate the measurement target gas, a light receiver configured to receive the laser light transmitted through the measurement target gas, and an analyzer configured to analyze the temperature and/or concentration of the measurement target gas based on an electric signal from the light receiver. In this case, when changing the wavelength of the laser light, the laser controller make the magnitude of the amplitude of the first laser light and the magnitude of the amplitude of the second laser light different from each other, and changes the intensity of the first laser light and the intensity of the second laser light in opposite directions.

PRIOR ART DOCUMENTS

Patent Documents

[Patent Document 1] Japanese Patent Laid-open Publication No. JP2008-051598A.
[Patent Document 2] Japanese Patent Laid-open Publication No. JP2011-158426A.
[Patent Document 3] Japanese Patent Laid-open Publication No. JP2015-040747A.

Non-Patent Documents

[Non-Patent Document 1] Maximilian Lackner, "Tunable diode laser absorption spectroscopy (TDLAS) in the process industries—a review," Reviews in Chemical Engineering, Vol. 23, Issue 2, April 2007.
[Non-Patent Document 2] Akihiro Murata, "Introduction of laser gas analyzer for process," Kangikyo, Japan Environmental Technology Association, pages 18 to 19, January 2010.

SUMMARY OF THE INVENTION

Problems to be Solved by the Invention

In the technologies disclosed in Patent Documents 1 to 3, it is not possible to remove the influence of the decrease in the laser light intensity due to contamination of a window provided in the optical path or the like. Specifically, when the measurement target gas is measured based on the absorption spectrum, it is important to detect the position (wavelength) and the size of the portion where the signal intensity decreases (hereinafter, also referred to as an "absorption line") appearing in the absorption spectrum. There is a case where the laser light with which the measurement target gas is irradiated fluctuates due to factors other than the original absorption such as contamination of a window provided in the optical path of the laser light, and in such a case, there is such a problem that the size of the portion where the signal intensity decreases (absorption line) appearing in the absorption spectrum is different from the case of the original absorption, and the analysis accuracy of the gas decreases.

In particular, Patent Document 3 has such a problem that it is difficult to achieve high sensitivity and high accuracy because minute variations occur in the mixed signals.

An object of the present invention is to provide a gas analyzer apparatus and a gas analysis method each capable of analyzing a gas with higher accuracy than that in the conventional technology.

Means for Solving the Problems

According to one aspect of the present invention, there is provided a gas analyzer apparatus including a laser light source, a laser controller, a photodetector unit, and an analyzer. The laser light source is configured to irradiate measurement target gas with laser light, and the laser controller is configured to control the laser light source to change a wavelength of the laser light in a predetermined wavelength band. The photodetector unit is configured to photoelectrically convert laser light having passed through the measurement target gas into an electric signal, and output the electric signal, and the analyzer configured to analyze an absorption wavelength of the measurement target gas based on the electric signal. The laser controller controls the laser light source such that an intensity of the laser light changes in a shape having a flat portion that is at least substantially constant in a predetermined time interval, and the wavelength of the laser light changes in the time interval.

Effect of the Invention

Therefore, according to the present invention, the laser controller controls the laser light source such that intensity of the laser light changes in a shape having a flat portion that is at least substantially constant in a predetermined time interval, and a wavelength of the laser light changes in the time interval. As a result, the detection accuracy of the gas analysis can be improved as compared with the conventional technology.

BRIEF DESCRIPTION OF THE DRAWINGS

FIG. 1A is a block diagram showing a configuration example of a gas analyzer apparatus 10 according to a first embodiment.

MODE FOR CARRYING OUT THE INVENTION

Figure 1B:
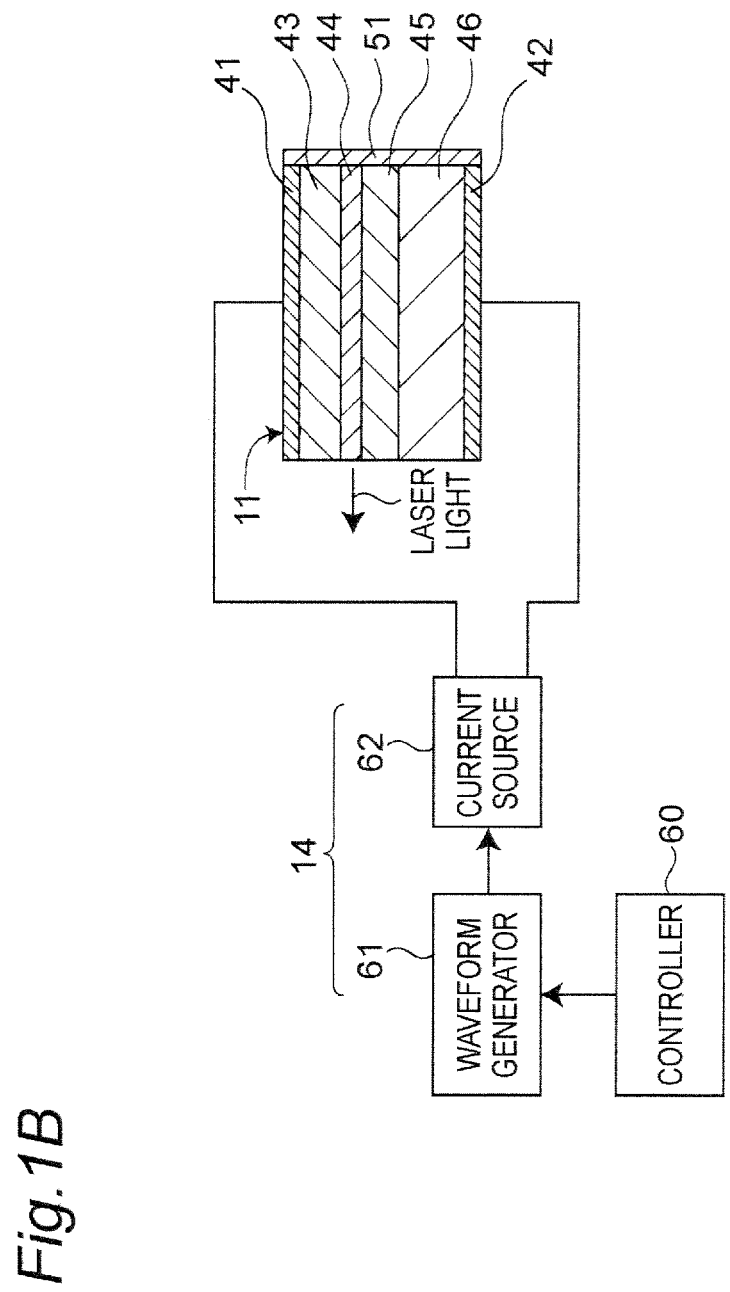
FIG. 1B is a block diagram showing details of a laser control apparatus 14 and a laser 11 in FIG. 1A.

Hereinafter, embodiments according to the present invention will be described with reference to the drawings. The same or similar components are denoted by the same reference numerals.

Features of Embodiments

In the embodiments and the modified embodiments according to the present invention, the concentration and temperature are detected by analyzing measurement target gas using the TDLAS method using a variable wavelength distribution active feedback (TDFB) type semiconductor laser. In this case, in the present embodiment, in particular, as will be described in detail later, for example, a laser light source is controlled such that intensity of laser light changes in a shape (for example, a rectangular shape or a trapezoidal shape) having at least a substantially constant flat portion in a predetermined time interval, and a wavelength of the laser light changes in the time interval.

First Embodiment

Configuration of Gas Analyzer Apparatus

Figure 2:
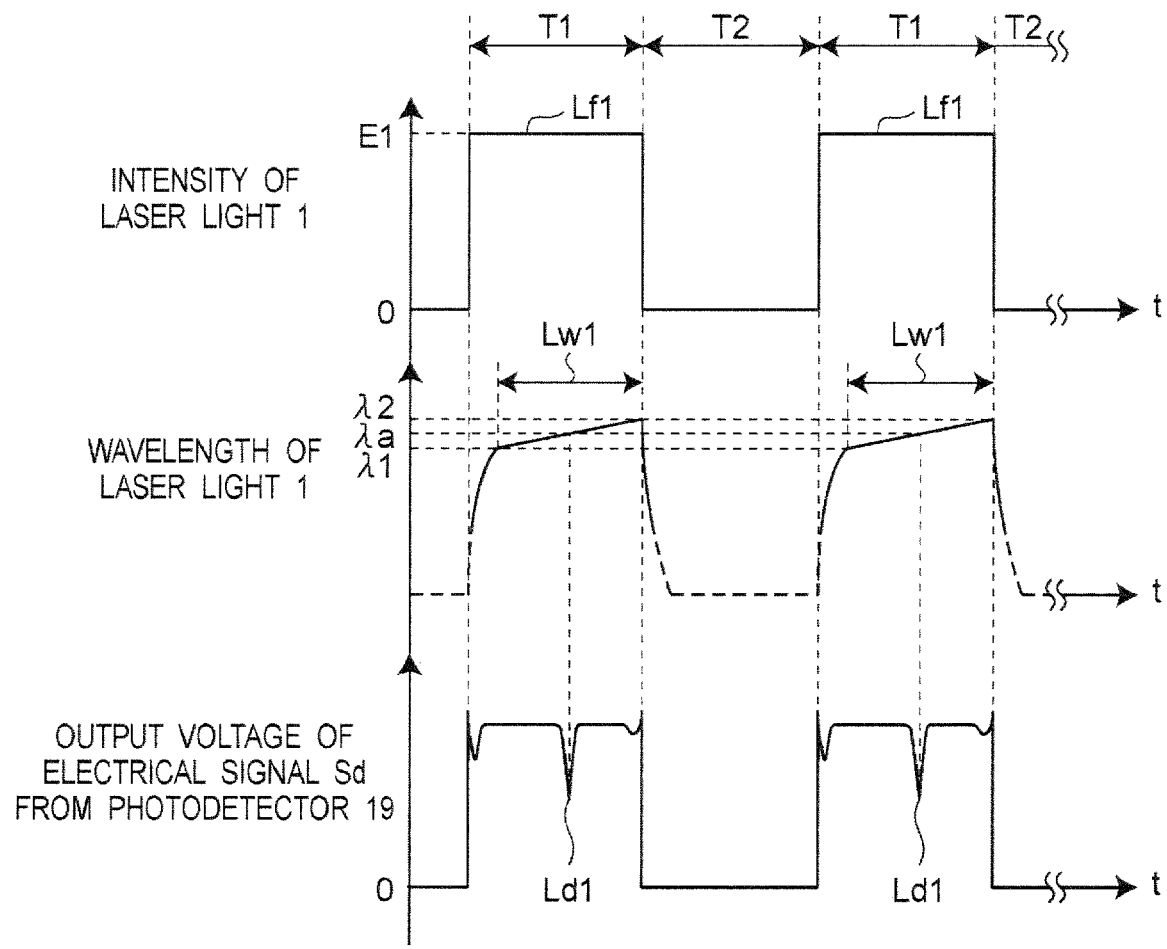
FIG. 2 is a diagram showing an operation of the gas analyzer apparatus 10 in FIG. 1A, and is a schematic waveform chart showing an intensity of laser light 1, a wavelength of the laser light 1, and an output voltage of an electric signal Sd from a photodetector unit 19.

FIG. 1A is a block diagram showing a configuration example of a gas analyzer apparatus 10 according to a first embodiment, and FIG. 1B is a block diagram showing details of a laser control apparatus 14 and a laser 11 in FIG. 1A. FIG. 2 is a diagram showing an operation of the gas analyzer apparatus 10 in FIG. 1A, and is a schematic waveform chart showing the intensity of the laser light 1, a wavelength of the laser light 1, and an output voltage of an electric signal Sd from a photodetector unit 19.

Referring to FIG. 1A, the gas analyzer apparatus 10 includes the semiconductor laser (hereinafter, referred to as a laser) 11 as a laser light source, the laser control apparatus 14, a collimator 17, the photodetector unit 19, an AC amplifier 21 that amplifies the electric signal Sd from the photodetector unit 19, and an analyzer apparatus 23. Note that, as will be described in detail later, the AC amplifier 21 is not limited to the AC amplifier, and may be any amplifier that can amplify the electric signal with reference to the flat portion where the intensity of the laser light is constant.

Referring to FIG. 1B, the laser control apparatus 14 includes a controller 60, a waveform generator 61, and a current power supply 62. The controller 60 controls the waveform generator 61 to set a time interval, a duty ratio, a voltage, and the like of a voltage signal generated by the waveform generator 61. In response, the waveform generator 61 generates a predetermined voltage signal having a rectangular or trapezoidal wave shape, for example, and outputs the voltage signal to the current power supply 62. The current power supply 62 includes a voltage/current conversion circuit, converts an input voltage signal into a predetermined drive current having a rectangular or trapezoidal wave shape, for example, and causes the drive current to flow between a pair of electrodes 41 and 42 of the laser 11.

In addition, in FIG. 1B, the laser 11 is configured such that a p-type cladding layer 43, an active layer 44, an n-type cladding layer 45, and an n-type substrate 46 are sandwiched between the pair of electrodes 41 and 42, and a reflecting surface 51 is formed on one side surface. In response to the current flowing through the pair of electrodes 41 and 42, the active layer 44 generates laser light, and the laser light reflected by the reflecting surface 51 is emitted in the lateral direction in FIG. 1B.

That is, the laser 11 is a laser light source capable of outputting the laser light 1 in a predetermined wavelength band, and in the present embodiment, the laser 11 is a known variable wavelength distribution active distribution feedback (TDFB) type semiconductor laser, and the same applies to lasers 12 and 13 described later. Generally, the TDFB laser can output laser light having a predetermined intensity by being inputted with an excitation current exceeding a threshold value current. In this case, the value of the current flowing through the laser 11 is changed by the drive current in the shape of, for example, a rectangular wave or a trapezoidal wave, so that the output of the laser light is changed. At this time, the temperature of the laser 11 is changed. As a result, the spacing between the diffraction gratings inside the laser 11 changes, so that the wavelength of the laser light changes.

In the present embodiment, the laser control apparatus 14 changes the excitation current value for the laser 11 in synchronization with a clock signal of a predetermined frequency to change the intensity of the laser light 1, for example, in a rectangular pulse shape with a duty ratio of 50% (the time interval T1=T2) as shown in FIG. 2. By controlling the laser 11 in this manner, the intensity of the laser light 1 becomes substantially constant at the maximum intensity E1 of the rectangular pulse in the time interval T1, and has a flat portion Lf1. In this case, the intensity variation of the flat portion Lf1 is preferably set to, for example, equal to or less than a threshold value of $10^{-6}$ with respect to the maximum intensity E1, for example, in order to improve accuracy for moisture detection in a semiconductor process apparatus to be described later.

At this time, the wavelength of the laser light 1 is slightly delayed from the rise of the light intensity, and monotonically increases and changes substantially proportionally with time in a wavelength scanning range Lw1 from a wavelength $\lambda 1$ to a wavelength $\lambda 2$, for example, as the temperature of the laser 11 rises. That is, the laser control apparatus 14 can control the laser 11 to output the laser light 1 from the laser 11 while temporally changing (scanning) the wavelength of the laser light 1.

In FIG. 2, in the illustration of the wavelength of the laser light 1, a dotted line indicates that the wavelength of the laser light 1 is not fixed and is indefinite, and the same applies to FIG. 4 described later. In this case, by setting the absorption wavelength of the measurement target gas between the wavelengths $\lambda 1$ and $\lambda 2$, a drop portion Ld1 of the output voltage of the electric signal Sd from the photodetector unit 19 generates at a predetermined wavelength $\lambda a$.

The laser light 1 from the laser 11 is emitted to the measurement target gas via the collimator 17 that collimates and converges the laser light 1, and then is inputted to the photodetector unit 19. The photodetector unit 19 receives the laser light transmitted through the measurement target gas, and photoelectrically converts the laser light into an analog electric signal Sd containing AC components according to the intensity of the received laser light. The AC amplifier 21 is an amplifier that has an amplification band (in particular, since the intensity of the laser light 1 rapidly increases or decreases, the laser light 1 has high-order harmonic components) capable of sufficiently amplifying the AC components of the electric signal Sd and can amplify the AC components with reference to the flat portion where the intensity of the laser light is constant. In particular, the AC amplifier 21 is configured to apply a predetermined offset to the electric signal Sd, for example, and amplify flat portions located on the left and right of the drop portion Ld1 at the output voltage of the electric signal Sd in FIG. 2 as a reference voltage of 0 V, for example. The AC amplifier 21 amplifies the analog electric signal Sd from the photodetector unit 19 as described above, and outputs an amplified electric signal Sda to the analyzer apparatus 23. Next, the analyzer apparatus 23 receives the analog electric signal Sda from the AC amplifier 21, performs AD conversion by a built-in AD converter, and then analyzes the waveform (absorption spectrum) of the electric signal Sda to analyze the concentration and temperature of the measurement target gas as known (see, for example, Non-Patent Documents 1 and 2). The analyzer apparatus 23 can be realized by, for example, a computer (information processing apparatus).

In the gas analyzer apparatus 10 configured as described above, the measurement target gas is irradiated with the laser light 1 while scanning the wavelength of the laser light 1 outputted from the laser 11 in a predetermined wavelength band of wavelengths $\lambda 1$ to $\lambda 2$ including the estimated absorption wavelength $\lambda a$, for example, and the concentration and temperature of the measurement target gas are measured by analyzing the absorption spectrum of the laser light according to the electric signal Sda including the absorption information of the measurement target gas obtained at that time. In this case, by repeating the rectangular pulse wave of the laser light 1, analysis integrated a plurality of times corresponding to a plurality of rectangular pulse waves is performed, and an average value thereof is calculated, and this leads to that the analysis accuracy can be improved.

The analyzer apparatus 23 analyzes the concentration and temperature of the measurement target gas based on the signal waveform of the input electric signal Sda. The analysis is performed by, for example, the following method. The analyzer apparatus 23 previously includes information on a theoretical value of a signal waveform of a measured light reception intensity signal (electric signal) for various concentrations and temperatures with respect to the measurement target gas. The analyzer apparatus 23 compares the signal waveform actually obtained by the measurement with the theoretical value of the signal waveform, and specifies the theoretical value of the signal waveform when the error is minimized. Then, by obtaining the concentration and temperature related to the specified theoretical value, measurement values of the concentration and temperature of the measurement target gas can be obtained.

The analysis of the gas concentration and the temperature is preferably synchronized based on a clock signal in the laser control apparatus 14. In this case, instead of the clock signal in the laser control apparatus 14, the clock signal may be reproduced from the received electric signal Sda, and the gas concentration and the temperature may be analyzed in synchronization with the reproduced clock signal.

Figure 7:
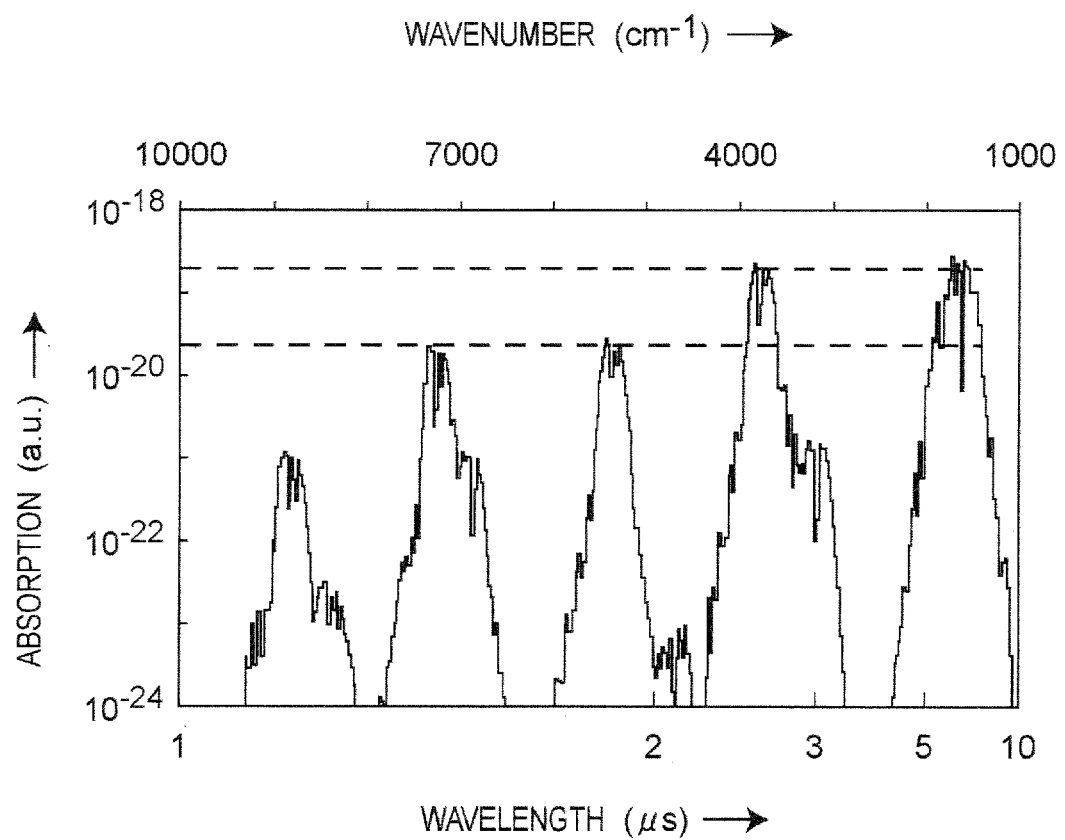
FIG. 7 is an absorption spectrum diagram showing wavelength characteristics of absorbance when target gas is $H_2O$ in the gas analyzer apparatuses 10, 10A, and 10B according to the first to third embodiments.

FIG. 7 is an absorption spectrum diagram showing wavelength characteristics of absorbance when the measurement target gas is $H_2O$ in the gas analyzer apparatus 10. An example of the relationship between the measurement target gas and an absorption wavelength $\lambda$ is shown in Table 1. The amplitude E1 of the intensity of the laser light 1 is set such that the wavelength $\lambda a$ corresponding to the drop portion Ld1 in FIG. 2 becomes the absorption wavelength shown in FIG. 7 or Table 1 within the wavelength scanning range Lw1.

TABLE 1

| Measured substance | Absorption wavelength [nm] |
| --- | --- |
| Water | 1390 |
| Carbon dioxide | 1960 |
| Carbon monoxide | 1570 |
| Carbon monoxide | 2330 |
| Nitrogen monoxide | 1800 |
| Nitrogen monoxide | 2650 |
| Nitrogen dioxide | 680 |
| Nitrous oxide | 2260 |
| Sulfur dioxide | 240 |
| Methane | 1650 |
| Acethylene | 1520 |
| Hydrogen fluoride | 1310 |
| Hydrogen chloride | 1790 |
| Hydrogen bromide | 1960 |
| Hydrogen iodide | 1540 |
| Hydrogen cyanide | 1540 |
| Hydrogen sulfide | 1570 |
| Ozone | 280 |
| Ammonia | 1500 |
| Formaldehyde | 1930 |
| Phosphine | 2150 |
| Oxygen | 760 |

As described above, according to the present embodiment, the laser control apparatus 14 changes the excitation current value for the laser 11 in synchronization with a clock signal of a predetermined frequency to change the intensity of the laser light 1 in a rectangular pulse shape as shown in FIG. 2, and at this time, the intensity of the laser light 1 becomes substantially constant at the maximum intensity E1 of the rectangular pulse in the time interval T1, and has the flat portion Lf1. At this time, the wavelength of the laser light 1 is slightly delayed from the rise of the light intensity, and changes substantially proportionally with time in the wavelength scanning range Lw1 from the wavelength $\lambda 1$ to the wavelength $\lambda 2$, for example, as the temperature of the laser 11 rises. That is, the laser control apparatus 14 can control the laser 11 to output the laser light 1 from the laser 11 while temporally changing (scanning) the wavelength of the laser light 1. In this case, by setting the absorption wavelength $\lambda a$ of the measurement target gas between the wavelengths $\lambda 1$ and $\lambda 2$, a drop portion Ld1 of the output voltage of the electric signal Sd from the photodetector unit 19 generates at a predetermined absorption wavelength $\lambda a$. By analyzing the electric signal Sda in the drop portion Ld1 as described above, the concentration and temperature of the measurement target gas can be measured.

That is, the laser control apparatus 14 controls the laser 11 such that the intensity of the laser light 1 changes in a rectangular shape having the amplitude E1 of the flat portion Lf1 that is at least substantially flat in the predetermined time interval T1, and the wavelength of the laser light 1 changes in the time interval T1. As a result, the detection accuracy and detection sensitivity of the gas analysis can be greatly improved as compared with the conventional technology. In addition, the gas analyzer apparatus 10 in FIG. 1A is configured using one laser, and the configuration can be simplified as compared with the gas analyzer apparatus of Patent Document 3 using two lasers.

Modified Embodiment of First Embodiment

In the first embodiment described above, it is set to that T1=T2, but by setting T1>T2, the wavelength scanning range Lw1 of the laser light 1 can be made larger than that in the case of T1=T2. However, as shown in FIG. 2, in the rise and fall of the intensity of the laser light 1, the wavelength of the laser light 1 slightly delays to reach the wavelength scanning range Lw1 and then goes out of the range via the wavelength scanning range Lw1. Therefore, the duty ratio of the intensity of the laser light 1 is desirably set to, for example, 80% or less. However, if the duty ratio is excessively lowered, the wavelength scanning range Lw1 becomes narrow, and thus, such a trade-off occurs, and for example, the duty ratio is preferably 30% or more.

In addition, by setting the absorption wavelength λa to a position approximately half the wavelength scanning range Lw1, the drop portion d1 of the output voltage can be set to a position approximately half the wavelength scanning range Lw1. As a result, the measurement target gas can be analyzed with high accuracy without being applied to the portion where the wavelength becomes indefinite.

Implementation Examples

Implementation Example According to First Embodiment

Figure 8:
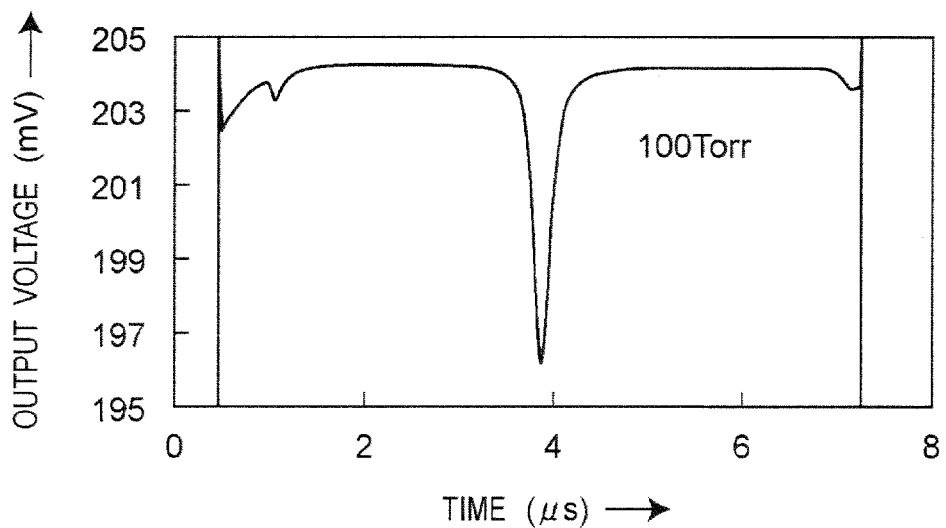
FIG. 8 is an experimental result of an implementation example of the gas analyzer apparatus 10 according to the first embodiment, and is a waveform chart showing an output voltage of the photodetector unit 19 when the target gas is $H_2O$ and the chamber pressure is 100 Torr.
Figure 9:
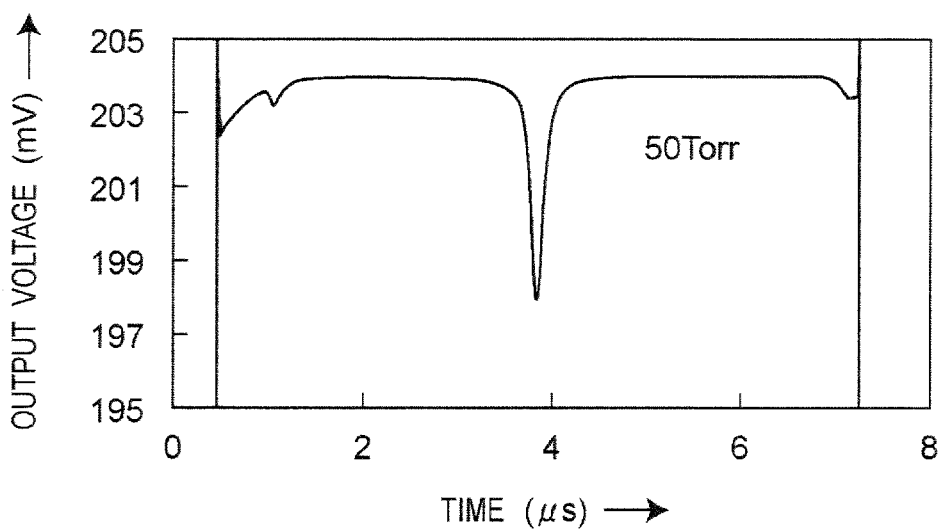
FIG. 9 is an experimental result of an implementation example of the gas analyzer apparatus 10 according to the first embodiment, and is a waveform chart showing an output voltage of the photodetector unit 19 when the target gas is $H_2O$ and the chamber pressure is 50 Torr.
Figure 10:
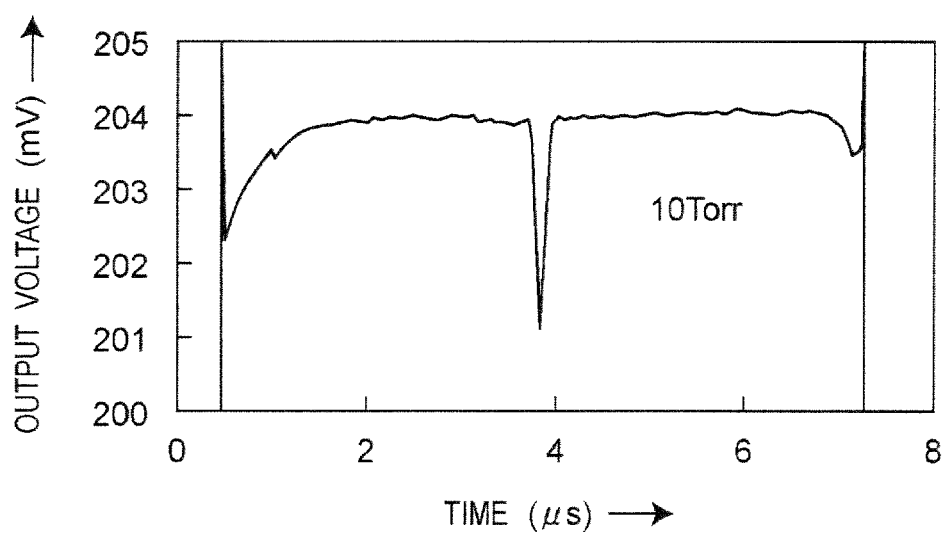
FIG. 10 is an experimental result of an implementation example of the gas analyzer apparatus 10 according to the first embodiment, and is a waveform chart showing an output voltage of the photodetector unit 19 when the target gas is $H_2O$ and the chamber pressure is 10 Torr.

FIGS. 8 to 10 are experimental results of an implementation example of the gas analyzer apparatus 10 according to the first embodiment, and are waveform charts of output voltages of the photodetector unit 19 when the target gas is $H_2O$ and the chamber pressure is 100 Torr, 50 Torr, and 10 Torr. In this case, specification conditions in the application test according to the implementation example are shown below.

Water vapor concentration: 0.7% (absolute concentration)
Temperature range: 300 K
Laser path length: 100 mm
Modulation frequency: 50 kHz
Number of integrations: 654 times (13 ms)
Laser wavelength: 1392.5 nm
Frequency band of AC amplifier 21: 20 MHz
AD converter in analyzer apparatus 23: Sampling frequency 100 MHz, 14 to 16 bits
Pressure: 10 Torr (1.3 kPa) to 100 Torr (103 kPa)
Atmospheric pressure equivalent concentration: 92 ppm As is clear from FIGS. 8 to 10, a drop portion Ld1 generates within the wavelength scanning range Lw1, and the analyzer apparatus 23 can analyze the measurement target gas.

In order to improve the sensitivity and the detection accuracy in the gas analyzer apparatus 10 according to the present embodiment, the following is conceivable.

(1) The integration time is set to one second, and is set to about ten times that of the conventional technology. In addition, the number of integrations is increased.

(2) A cooling type photodetector unit is used as the photodetector unit 19, and a cooling type photodetector unit whose detection sensitivity is about ten times that of the conventional technology is used.

(3) The amplification degree of the AC amplifier 21 is set to about ten times that of the conventional technology.

(4) The intensity of the laser light 1 from the laser 11 is set to about ten times that in the conventional technology.

(5) Noise in other electric circuits is reduced as compared with the conventional technology.

Second Embodiment

Figure 3:
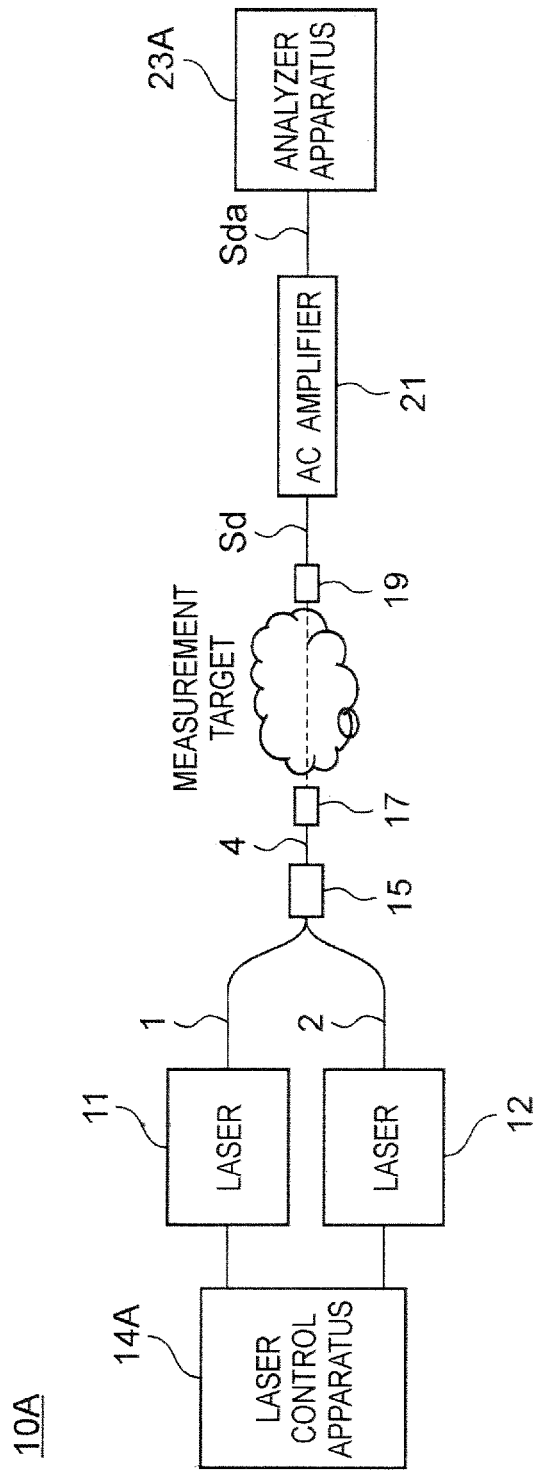
FIG. 3 is a block diagram showing a configuration example of a gas analyzer apparatus 10A according to a second embodiment.

FIG. 3 is a block diagram showing a configuration example of a gas analyzer apparatus 10A according to a second embodiment. FIG. 4 is a diagram showing an operation of the gas analyzer apparatus 10A in FIG. 3, and is a schematic waveform chart showing the intensities of the laser lights 1 and 2, wavelengths of the laser lights 1 and 2, and an output voltage of the electric signal Sd from the photodetector unit 19. The gas analyzer apparatus 10A according to the second embodiment is different from the gas analyzer apparatus 10 according to the first embodiment in FIG. 1A in the following points.

(1) The laser 12 that emits laser light 2 is further provided.

(2) Instead of the laser control apparatus 14, a laser control apparatus 14A that controls the two lasers 11 and 12 is provided. The laser control apparatus 14A includes the controller 60 in FIG. 1B, two signal generators 61 (FIG. 1B), and two current power supplies 62 (FIG. 1B).

(3) A multiplexer 15 is provided between the lasers 11 and 12 and the collimator 17.

(4) Instead of the analyzer apparatus 23, an analyzer apparatus 23A that analyzes each portion of the electric signals corresponding to the two beams of the laser light 1 and 2 in a time division manner is provided.

Differences will be described below.

Figure 4:
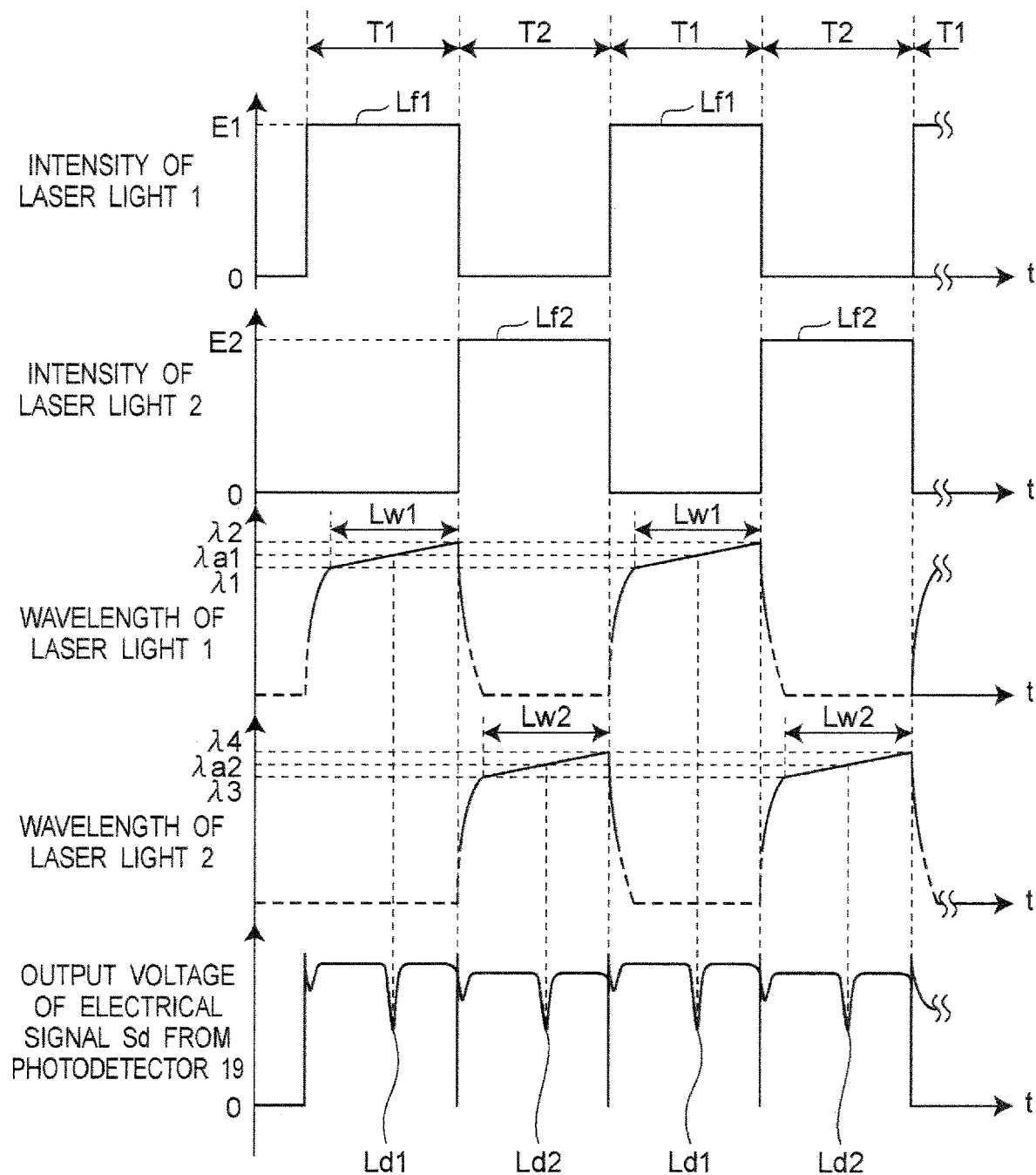
FIG. 4 is a diagram showing an operation of the gas analyzer apparatus 10A in FIG. 3, and is a schematic waveform chart showing intensities of laser light 1 and laser light 2, wavelengths of the laser lights 1 and 2, and an output voltage of the electric signal Sd from the photodetector unit 19.

The laser control apparatus 14A changes the excitation current value for the laser 11 in synchronization with a clock signal of a predetermined frequency to change the intensity of the laser light 1, for example, in a rectangular pulse shape with a duty ratio of 50% (the time interval T1=T2) as shown in FIG. 4. By controlling the laser 11 in this manner, the intensity of the laser light 1 becomes substantially constant at the maximum intensity E1 of the rectangular pulse in the time interval T1, and has a flat portion Lf1.

In addition, the laser control apparatus 14A changes the excitation current value for the laser 12 in synchronization with the inverted clock signal generated by inverting the clock signal to change the intensity of the laser light 2, for example, in a rectangular pulse shape with a duty ratio of 50% (the time interval T1=T2) as shown in FIG. 4. By controlling the laser 12 in this manner, the intensity of the laser light 2 becomes substantially constant at the maximum intensity E2 of the rectangular pulse in the time interval T2, and has a flat portion Lf2.

That is, as shown in FIG. 4, the laser control apparatus 14A alternately repeats the laser light 1 and the laser light 2 to control the lasers 11 and 12 to change the intensities in a rectangular pulse shape having substantially the same maximum intensities E1 and E2 (E1≈E2). In this case, the intensities of E1 and E2 can be obtained from the difference between the maximum intensities E1 and E2, and control is performed as follows.

(1) The intensity variation of each of the flat portions Lf1 and Lf2 is preferably set to, for example, equal to or less than a threshold value of $10^{-6}$ with respect to the maximum intensities E1 and E2, for example, in order to improve accuracy for moisture detection in the semiconductor process apparatus to be described later.

(2) The difference between E1 and E2 is preferably set to be equal to or less than a threshold value of $10^{-6}$, for example, with respect to the maximum intensities E1 and E2.

At this time, in a manner similar to that of the first embodiment, the wavelength of the laser light 1 is slightly delayed from the rise of the light intensity, and monotonically increases and changes substantially proportionally with time in the wavelength scanning range Lw1 from the wavelength λ1 to the wavelength λ2, for example, as the temperature of the laser 11 rises. That is, the laser control apparatus 14A can control the laser 11 to output the laser light 1 from the laser 11 while temporally changing (scanning) the wavelength of the laser light 1.

In addition, the wavelength of the laser light 2 is slightly delayed from the rise of the light intensity, and monotonically increases and changes substantially proportionally with time in a wavelength scanning range Lw2 (Lw1≈Lw2, but may be slightly different) from the wavelength λ3 to the wavelength λ4, for example, as the temperature of the laser 12 rises. That is, the laser control apparatus 14A can control the laser 12 to output the laser light 2 from the laser 11 while temporally changing (scanning) the wavelength of the laser light 1.

In this case, by setting the absorption wavelength of first measurement target gas between the wavelengths λ1 and λ2 related to the laser light 1, a drop portion d1 of the output voltage of the electric signal Sd from the photodetector unit 19 generates at a predetermined wavelength λa1. In addition, by setting the absorption wavelength of second measurement target gas between the wavelengths λ3 to λ4 related to the laser light 2, a drop portion Ld2 of the output voltage of the electric signal Sd from the photodetector unit 19 generates at a predetermined wavelength λa2 (λa1≈λa2, but may be slightly different from each other).

After the two beams of the laser light 1 and 2 from the lasers 11 and 12 are multiplexed by the multiplexer 15, the multiplexed light 4 is emitted to the measurement target gas via the collimator 17 that collimates and converges the multiplexed light 4, and then is inputted to the photodetector unit 19. The photodetector unit 19 receives the laser light transmitted through the measurement target gas, and photoelectrically converts the laser light into an analog electric signal Sd containing AC components according to the intensity of the received laser light. The AC amplifier 21 has an amplification band (in particular, since the intensity of the laser light 1 rapidly increases or decreases, the laser light 1 has high-order harmonic components) capable of sufficiently amplifying the AC components of the electric signal Sd, amplifies the analog electric signal Sd from the photodetector unit 19, and outputs the amplified electric signal Sda to the analyzer apparatus 23. Next, the analyzer apparatus 23 receives the analog electric signal Sda from the AC amplifier 21, performs AD conversion by a built-in AD converter, and then analyzes the waveform (absorption spectrum) of the electric signal Sda to analyze the concentration and temperature of the measurement target gas as known (see, for example, Non-Patent Documents 1 and 2). The analyzer apparatus 23 can be realized by, for example, a computer (information processing apparatus).

In this case, the analyzer apparatus 23A according to the second embodiment performs analysis processing of the gas concentration and the temperature by time-division processing on the electric signal Sda in synchronization with a clock signal in the laser control apparatus 14 or a clock signal reproduced by the analyzer apparatus 23A. That is, the analysis processing (including signal integration) related to the measurement target gas having the absorption wavelength λa1 is executed in the time interval T1, and the analysis processing (including signal integration) related to the measurement target gas having the absorption wavelength λa2 is executed in the time interval T2. As a result, analysis for two measurement target gases can be performed substantially simultaneously.

In the gas analyzer apparatus 10A configured as described above, the measurement target gas is irradiated with the laser light 1 while scanning the wavelength of the laser light 1 outputted from the laser 11 in a predetermined wavelength band of the wavelengths λ1 to λ2 including the estimated absorption wavelength λa1, for example, and the measurement target gas is irradiated with the laser light 2 while scanning the wavelength of the laser light 2 outputted from the laser 12 in a predetermined wavelength band of the wavelengths λ3 to λ4 including the estimated absorption wavelength λa2, for example. The concentration and temperature of the measurement target gas are measured by analyzing the absorption spectrum of the laser light according to the electric signal Sda including the absorption information of the measurement target gas obtained at that time. In this case, by repeating the rectangular pulse waves of the laser lights 1 and 2, analysis integrated a plurality of times corresponding to the plurality of rectangular pulse waves of the laser lights 1 and 2 is performed, and an average value thereof is calculated, and this leads to that the analysis accuracy can be improved.

In addition, as in the second embodiment, by irradiating the target gas with the multiplexed light obtained by multiplexing the two beams of the laser light 1 and 2 having the maximum intensities E1 and E2 different from each other to obtain the absorption spectrum, it is possible to detect the change in the absorption amount with high accuracy with a simple configuration as compared with the conventional technology. In addition, the number of integrations per predetermined time can be doubled, and the analysis accuracy can be improved as compared with the conventional technology.

Modified Embodiment of Second Embodiment

In the second embodiment described above, the same measurement target gas is analyzed in substantially the same absorption wavelength band with E1≈E2, but the present invention is not limited thereto, and measurement target gases different from each other in different absorption wavelength bands may be analyzed with E1 #E2. In this case, in addition to the laser light in the wavelength band including the wavelength absorbing the gas component, the laser light in the wavelength band including the wavelength absorbing the gas component different from the measurement target gas component is used, so that the plurality of gas components can be simultaneously measured. In this case, in order to analyze different measurement target gases in the time intervals T1 and T2 in the analyzer apparatus 23A, the wavelength scanning ranges Lw1 and Lw2 are preferably set such that the absorption wavelength λa1 of one measurement target gas exists in the wavelength scanning range Lw1 and the absorption wavelength λa2 of the measurement target gas exists in the wavelength scanning range Lw2.

In the second embodiment described above, it is set to that T1=T2, but T1≠T2 may be satisfied. Thus, the wavelength scanning range Lw1 of the laser light 1 and the wavelength scanning range Lw2 of the laser light 2 may be made different from each other. However, as described in the modified embodiment of the first embodiment, the wavelength scanning ranges Lw1 and Lw2 are preferably set in consideration of the duty ratio of the rectangular pulse wave.

In addition, by setting the absorption wavelength λa1 to a position approximately half the wavelength scanning range Lw1, the drop portion d1 of the output voltage can be set to a position approximately half the wavelength scanning range Lw1. By setting the absorption wavelength λa2 to a position approximately half the wavelength scanning range Lw2, the drop portion Ld2 of the output voltage can be set to a position approximately half the wavelength scanning range Lw2. As a result, the measurement target gas can be analyzed with high accuracy without being applied to the portion where the wavelength becomes indefinite.

Third Embodiment

Figure 5:
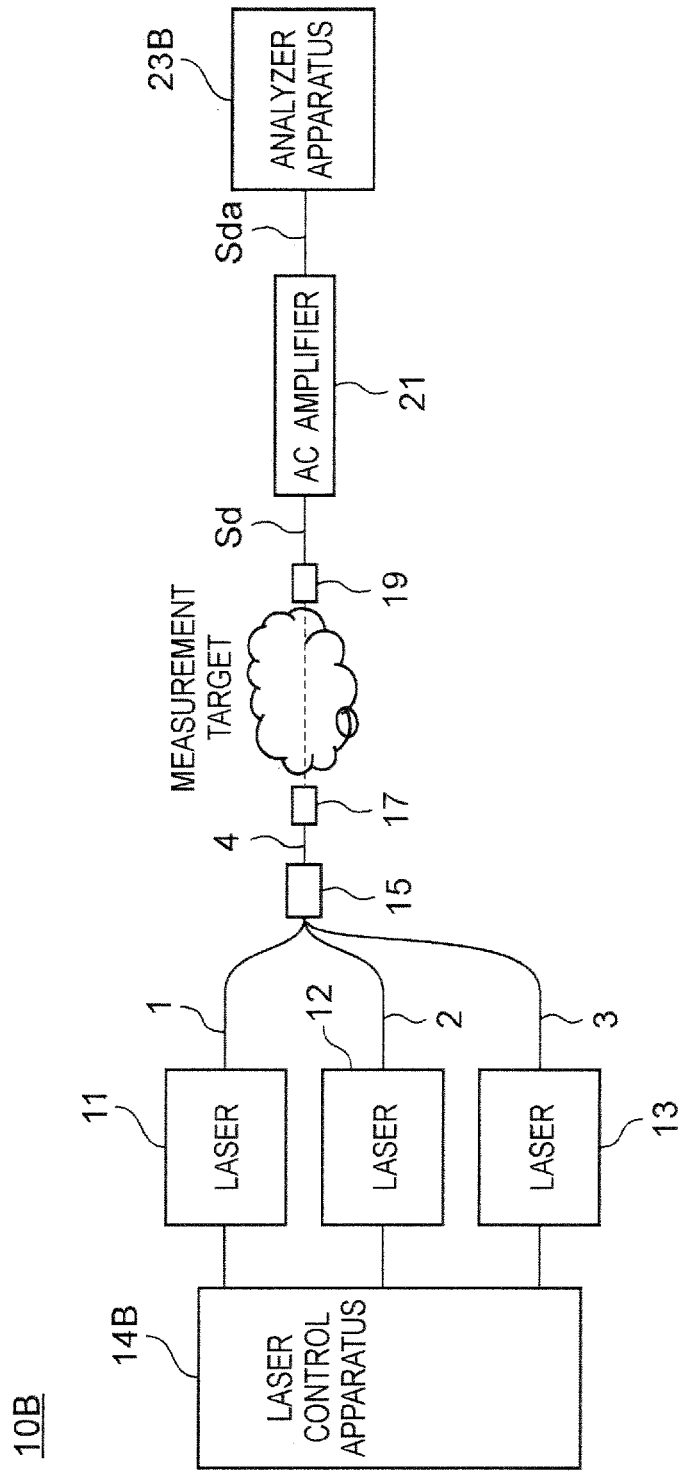
FIG. 5 is a block diagram showing a configuration example of a gas analyzer apparatus 10B according to a third embodiment.

FIG. 5 is a block diagram showing a configuration example of a gas analyzer apparatus 10B according to a third embodiment. The gas analyzer apparatus 10B according to the third embodiment is different from the gas analyzer apparatus 10A according to the second embodiment in FIG. 3 in the following points.

(1) The laser 13 that emits laser light 3 is further provided.

(2) Instead of the laser control apparatus 14A, a laser control apparatus 14B that controls the three lasers 11, 12, and 13 is provided.

(3) Instead of the analyzer apparatus 23A, an analyzer apparatus 23B is provided that analyzes each portion of the electric signals corresponding to the three beams of the laser light 1, 2, and 3 in a time division manner.

With the above configuration, by repeating emission of the rectangular pulse waves of the laser lights 1, 2, and 3, sequentially, so as not to overlap each other, the analysis integrated or accumulated a plurality of times corresponding to the plurality of rectangular pulse waves of the laser lights 1, 2, and 3 is performed, and the average value thereof is calculated, and this leads to that the analysis accuracy can be improved.

In this case, the maximum intensities E1, E2, and E3 of the laser lights 1, 2, and 3 may be the same as each other, or may be set to be different from each other, or at least two of the maximum intensities E1, E2, and E3 may be set to be the same as each other. As a result, the wavelength bands including the absorption wavelength corresponding to the wavelength setting range can be set to be the same as or different from each other, or at least two of the wavelength bands can be set to be the same as each other.

In addition, the time intervals E1, E2, and E3 of the laser lights 1, 2, and 3 may be the same as each other, or may be set to be different from each other, or at least two of the time intervals E1, E2, and E3 may be set to be the same as each other. However, it is similar to the second embodiment that the wavelength scanning range changes depending on the lengths of the time intervals E1, E2, and E3, and the same applies to the notes regarding the setting in the second embodiment.

In the third embodiment, the three beams of the laser light 1, 2, and 3 are multiplexed using the three lasers 11, 12, and 13, but the present invention is not limited thereto, and four beams of the laser light may be multiplexed using four or more lasers to analyze, for example, four or more different measurement target gases.

Modified Embodiment of First to Third Embodiments

Figure 6:
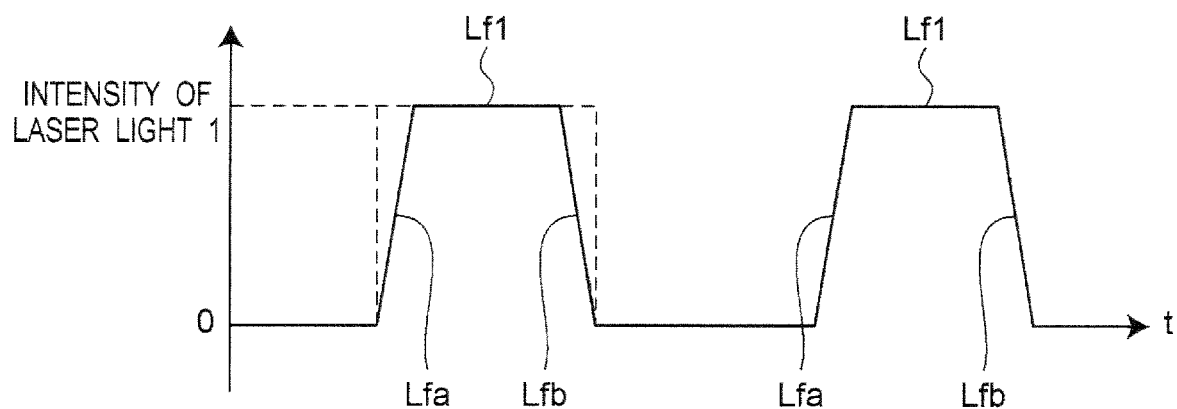
FIG. 6 is a waveform chart showing the intensity of the laser light 1 according to a modified embodiment of the first to third embodiments.

FIG. 6 is a waveform chart showing the intensity of the laser light 1 according to a modified embodiment of the first to third embodiments. As shown in FIG. 6, the laser 11 or the like may be controlled to have a trapezoidal shape instead of the rectangular shape of the intensity of the laser light 1 or the like. This is widely applicable to the first to third embodiments and its modified embodiments.

However, in order to make the wavelength scanning range Lw1 as long as possible, a rising portion Lfa and a falling portion Lfb of the trapezoid preferably rise or fall rapidly by increasing the inclination thereof. One of the rising portion Lfa and the falling portion Lfb of the trapezoid may be formed at an angle of substantially 90 degrees or −90 degrees.

Fourth Embodiment

Figure 11:
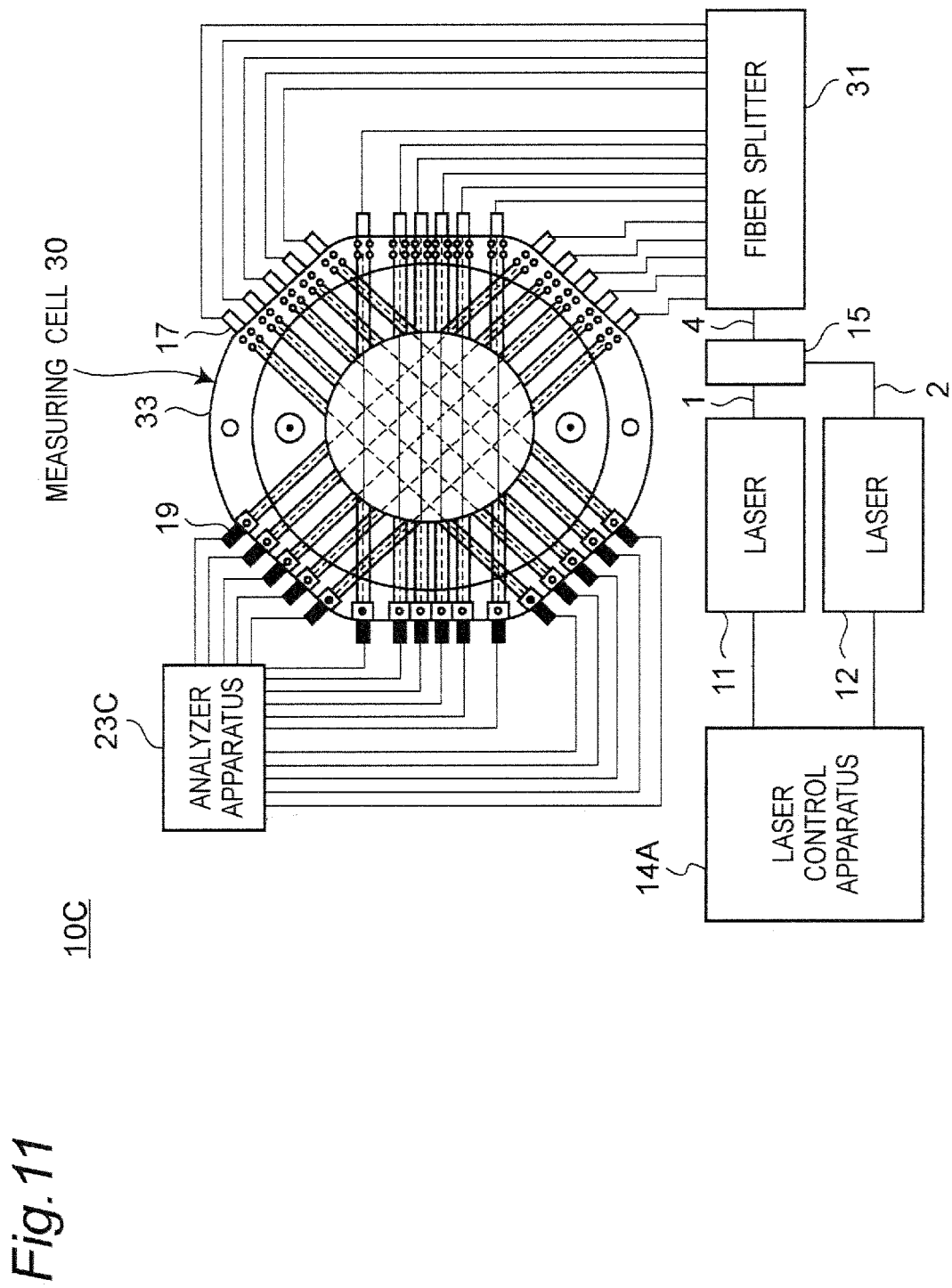
FIG. 11 is a block diagram showing a configuration example of a two-dimensional gas analyzer apparatus 10C according to a fourth embodiment.

FIG. 11 is a block diagram showing a configuration example of a two-dimensional gas analyzer apparatus 10C according to a fourth embodiment. In the first to third embodiments, the configurations of the gas analyzer apparatuses 10, 10A, and 10B that have one path (optical path) and measure the state of the measurement target gas one-dimensionally have been described. In the fourth embodiment, the configuration of the two-dimensional gas analyzer apparatus will be described that enables measurement in a plurality of paths in order to enable two-dimensional measurement of the concentration and temperature of the measurement target gas.

X-ray computed tomography (CT), which is generally well known, is a technology in which an object is scanned using an X-ray, the inside of the cross section is subdivided, an X-ray absorption amount is measured for each segmented element, and information of the same number of X-ray absorption amounts as an unknown number is collected to constitute the cross section of the object. When the measurement target gas contains a large amount of components such as water vapor and carbon dioxide, the emitted light is partially absorbed and attenuated at a certain wavelength when passing through these chemical species having a unique absorption spectrum. In the absorption method, an absorption amount is measured as an integral value of an optical path passing through a measurement field. A two-dimensional temperature distribution can be measured by irradiating a measurement field with a plurality of beams of laser light and reconstructing a two-dimensional image using a CT technology.

Configuration of Two-Dimensional Gas Analyzer Apparatus

The two-dimensional gas analyzer apparatus 10C in FIG. 11 is a two-dimensional gas analyzer apparatus capable of two-dimensionally measuring the concentration and temperature of measurement target gas, and includes two lasers 11 and 12, the laser control apparatus 14A, the multiplexer 15, a fiber splitter 31, a measurement cell 30, and an analyzer apparatus 23C. In this case, it is assumed that the AC amplifier 21 is built in the analyzer apparatus 23C.

The measurement cell 30 has an opening and has a substantially circular frame 33. In order to measure transmitted light intensities of sixteen optical paths (paths), sixteen collimators 17 and sixteen photodetectors 19 provided to face the collimators 17 are attached to the frame 33. Therefore, in the opening of the measurement cell 30, a pair of the collimator 17 and the photodetectors 19 form a path (optical path). That is, the measurement cell 30 has sixteen paths (optical paths). Each path (optical path) is configured to be included in the same plane, and two-dimensional measurement can be performed in this plane. Hereinafter, the normal direction of the plane including each path (optical path) is referred to as a "normal direction of the measurement cell 30".

The measurement cell 30 having such a configuration is arranged in a measurement field including measurement target gas, and the two-dimensional gas analyzer apparatus 10C measures gas components in an opening region of the measurement cell 30.

The laser 11 outputs the laser light 1 in the wavelength band including the absorption wavelength $\lambda a1$ absorbed by the component of the first measurement target gas, and the laser 12 outputs the laser light 2 in the wavelength band including the specific wavelength λa2 at which the component of the first measurement target gas is not absorbed or the absorption wavelength λa2 absorbed by the component of the second measurement target gas different from the component of the first measurement target gas. In addition, the laser 11 and the laser 12 output the laser light 1 and the laser light 2 having different intensity change directions or different maximum intensities E1 and E2.

The laser lights 1 and 2 respectively emitted from the laser 11 and the laser 12 are inputted to the multiplexer 15 and multiplexed, and the multiplexed light is inputted to the fiber splitter 31. The fiber splitter 31 splits the multiplexed light into sixteen split light and inputs the split light to each of the sixteen collimators 17. Each split light is emitted to the measurement field via the collimator 17. The laser light transmitted through the measurement field is received by each of the photodetectors 19, photoelectrically converted into an electric signal, and then it is inputted to the analyzer apparatus 23.

The analyzer apparatus 23 analyzes the signal waveform of the electric signal from each of the photodetectors 19 to reconstruct a two-dimensional image showing the concentration and/or temperature distribution of the gas components. The reconstruction of the two-dimensional image can be performed using an existing CT technology.

In the fourth embodiment described above, the number of paths (optical paths) is sixteen, but the number of paths (optical paths) is not limited to sixteen, and may be eight, twelve, or the like.

According to the two-dimensional gas analyzer apparatus 10C of the fourth embodiment configured as described above, it is possible to two-dimensionally measure the temperature and concentration distribution of the measurement target gas. In particular, by making a difference between the amplitudes of the two beams of the laser light, it is possible to cancel the effect of attenuating the laser light intensity due to the effect other than the original absorption of the target gas components, such as contamination of a window, and it is possible to prevent decrease in the gas analysis accuracy.

Application Examples

Hereinafter, application examples of the two-dimensional gas analyzer apparatus 10C according to the fourth embodiment will be described. In the following application examples, the gas analyzer apparatuses 10 to 10B according to the first to fourth embodiments may be used.

Application Example 1

Figure 12:
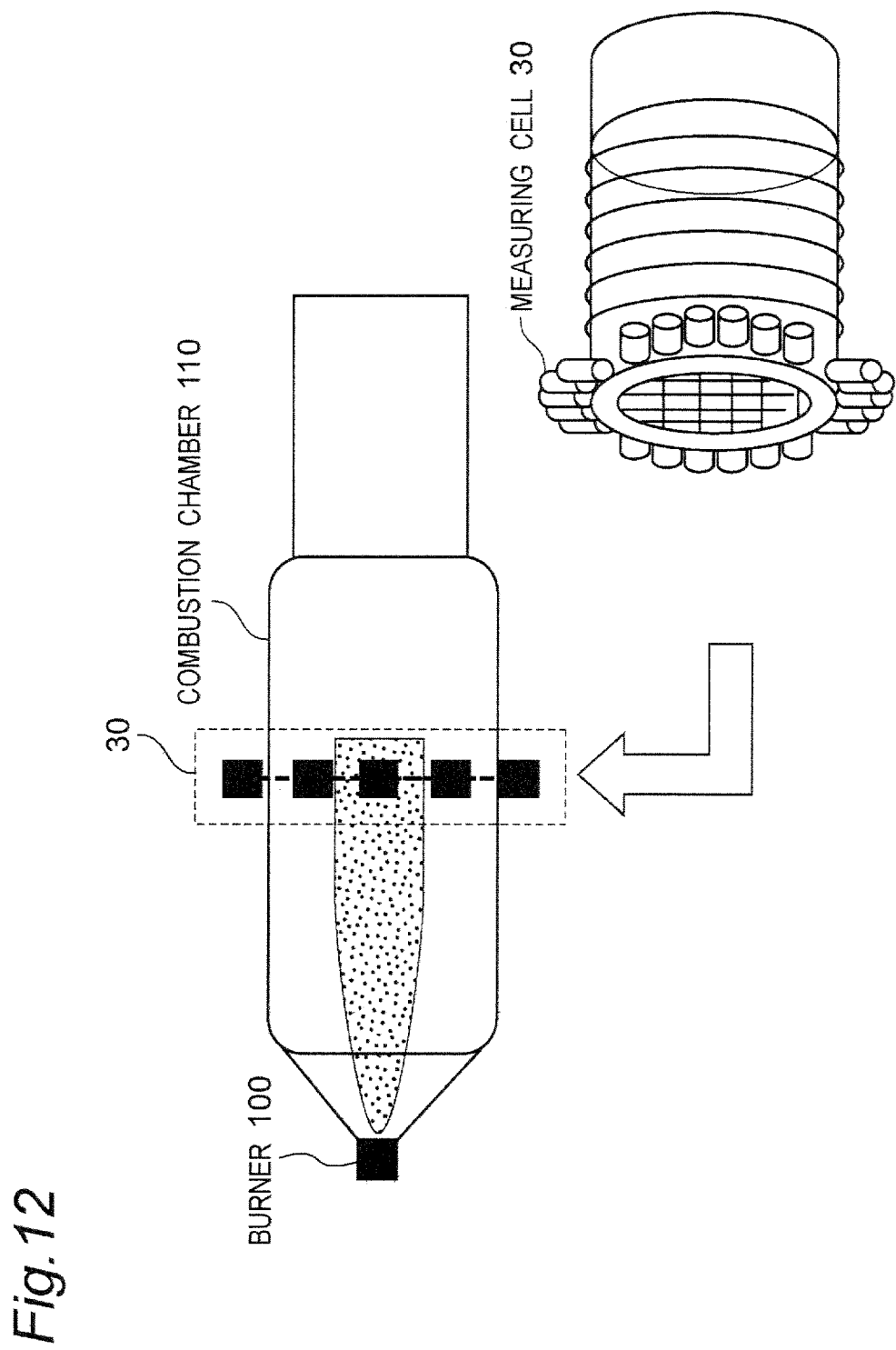
FIG. 12 is a schematic view showing Application Example 1 of the two-dimensional gas analyzer apparatus 10C in FIG. 11 to a burner 100.

FIG. 12 is a schematic view showing Application Example 1 of the two-dimensional gas analyzer apparatus 10C in FIG. 11 to a burner 100.

As shown in FIG. 12, the two-dimensional gas analyzer apparatus 10C can be applied to detection of a combustion state (temperature and concentration of target gas) in a combustion chamber of the boiler burner 100 used in a thermal power plant or the like. For example, by disposing the measurement cell 30 in FIG. 11 in a combustion chamber 110 of the boiler, the combustion state in the combustion chamber 110 of the burner 100 can be two-dimensionally grasped. Furthermore, by arranging a plurality of measurement cells 30 in the normal direction with respect to the combustion chamber 110, it is also possible to three-dimensionally measure the combustion state.

Application Example 2

Figure 13:
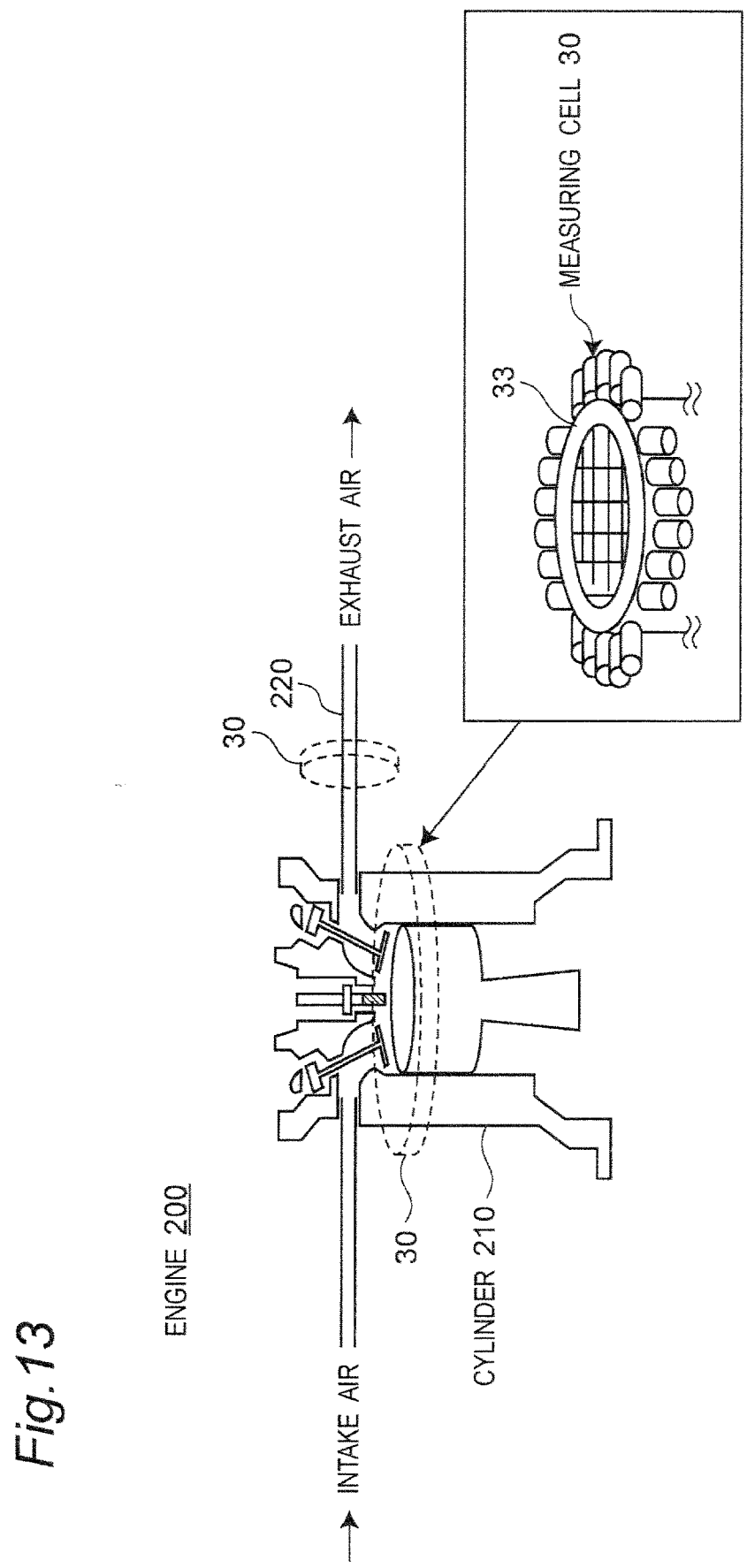
FIG. 13 is a schematic diagram showing Application Example 2 of the two-dimensional gas analyzer apparatus 10C in FIG. 11 to an engine 200.

FIG. 13 is a schematic diagram showing Application Example 2 of the two-dimensional gas analyzer apparatus 10C in FIG. 11 to an engine 200.

As shown in FIG. 13, the two-dimensional gas analyzer apparatus 10C can be applied to detection of a combustion state (temperature and concentration of target gas) of a vehicle engine. As shown in FIG. 13, for example, by providing the measurement cell 30 in FIG. 11 in a cylinder 210 of the engine 200, it is possible to detect the combustion state inside the cylinder 210. In addition, the measurement cell 30 in FIG. 11 may be provided in an exhaust pipe 220 which is a flow path of the exhaust gas discharged from the cylinder 210. This makes it possible to detect the temperature and concentration of the exhaust gas. In addition, it is also possible to three-dimensionally measure the state of the gas by arranging a plurality of measurement cells 30 in FIG. 11 in the normal direction in the cylinder 210 or the exhaust pipe 220.

According to Application Example 2 configured as described above, it is possible to detect the temperature and concentration of various gases in the cylinder 210 or the exhaust system of the engine 200, and it is useful for elucidating the transient phenomenon of combustion and the unburned fuel discharge behavior.

Application Example 3

Figure 14:
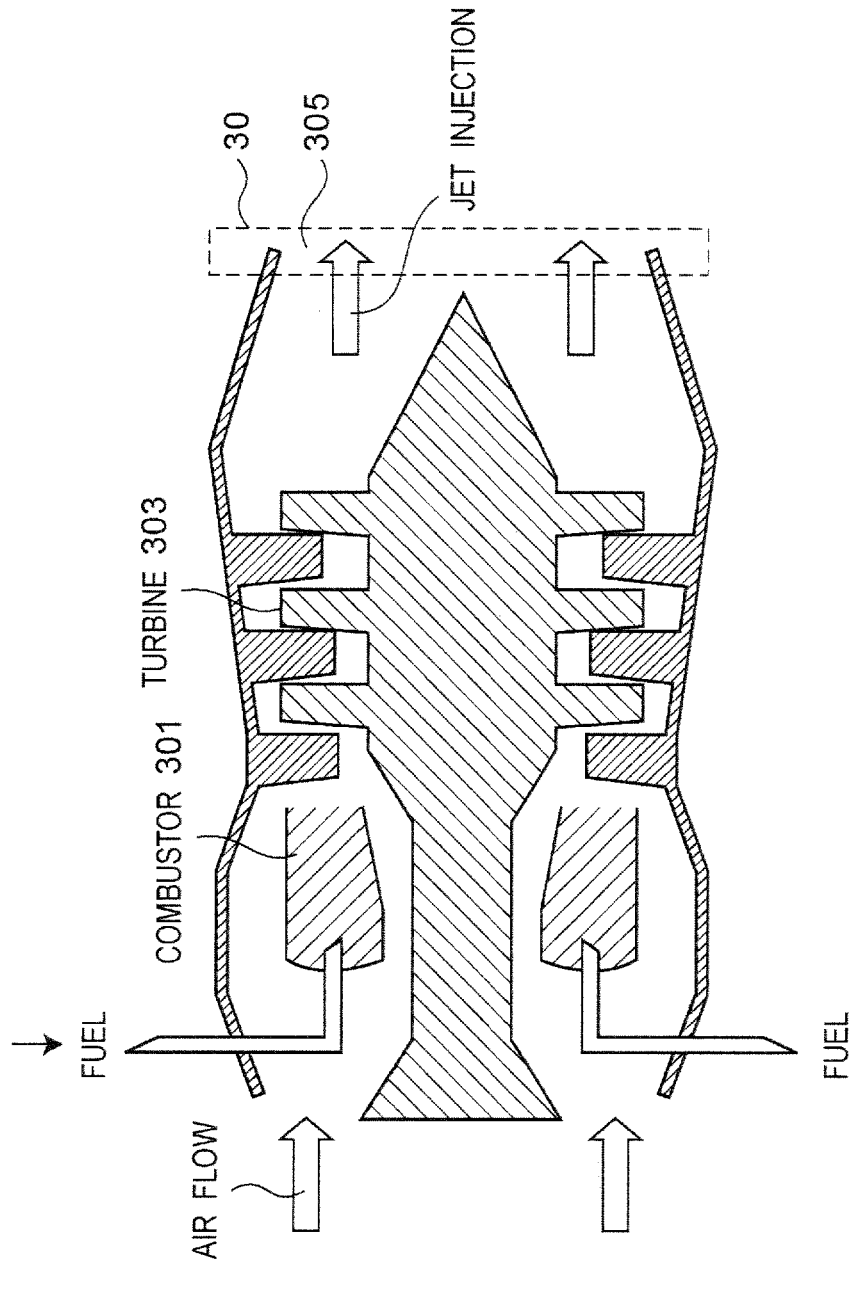
FIG. 14 is a schematic diagram showing Application Example 3 of the two-dimensional gas analyzer apparatus 10C in FIG. 11 to a jet engine 300.

FIG. 14 is a schematic diagram showing Application Example 3 of the two-dimensional gas analyzer apparatus 10C in FIG. 11 to a jet engine 300.

As shown in FIG. 14, the two-dimensional gas analyzer apparatus 10C can be applied to detection of a combustion state (temperature and concentration of target gas) of a jet engine or an industrial gas turbine. In the jet engine 300 (or gas turbine), the introduced airflow is compressed by a compressor driven by the rotational force of a turbine 303, mixed with fuel in a combustor 301, and burned. The combustion gas generated by combustion rotates the turbine 303 and is exhausted to the outside from an injection port. For example, as shown in FIG. 13, the measurement cell 30 may be provided in the vicinity of an injection port 305 of the jet engine 300. This makes it possible to detect the combustion state inside the combustor 301 of the jet engine 300. Such a technology is useful for elucidating a vibration phenomenon due to a flow field and fuel inhomogeneity. In addition, a plurality of measurement cells 30 in FIG. 11 may be arranged in the exhaust direction of the combustion gas in the vicinity of the injection port 305. As a result, the combustion state can be three-dimensionally detected.

According to Application Example 3 configured as described above, by applying the configuration of the gas analyzer apparatus in which the CT technology and the laser are combined to a method of measuring the temperature distribution and the concentration distribution in two or three dimensions, it is possible to apply and develop the gas analyzer apparatus to combustion equipment such as a boiler, an engine, and a gas turbine while achieving simplification, quantification, and high sensitivity of the apparatus.

Application Example 4

Figure 15:
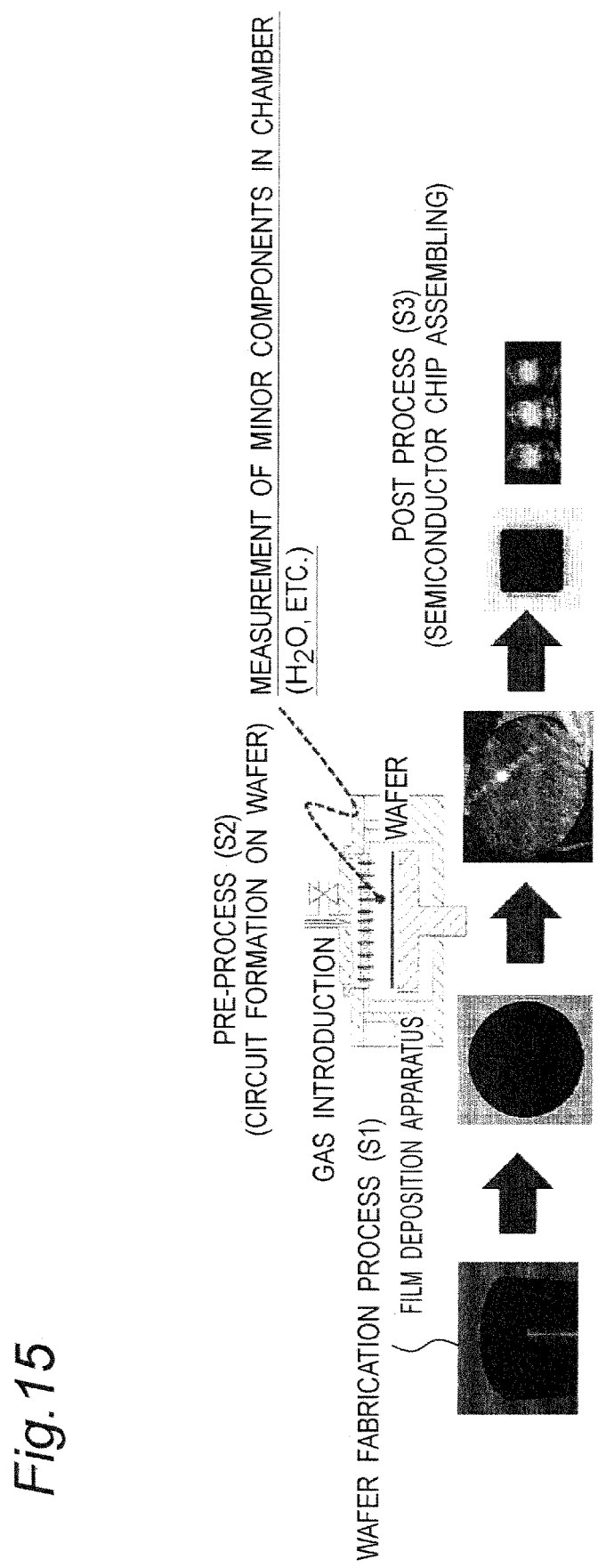
FIG. 15 is a schematic diagram showing Application Example 4 of the two-dimensional gas analyzer apparatus 10C in FIG. 11 to semiconductor process processing.
Figure 16:
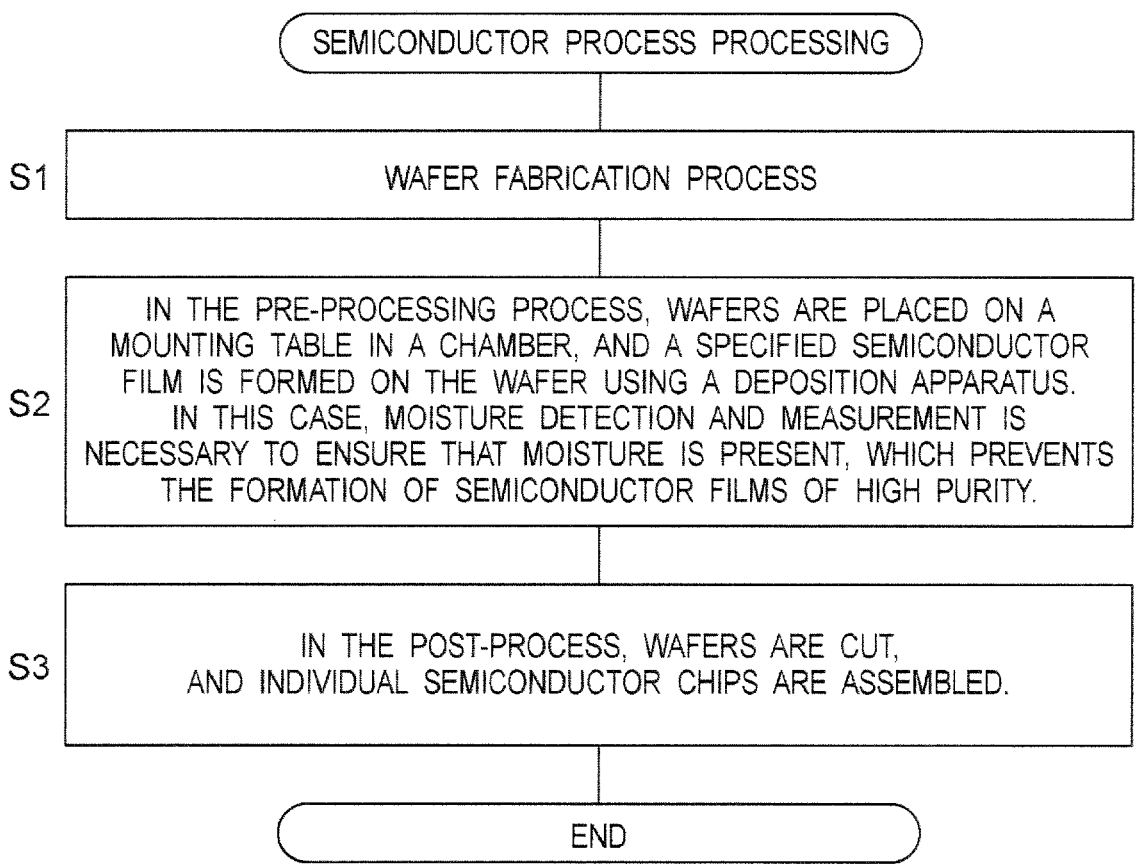
FIG. 16 is a flowchart showing Application Example 4 of FIG. 15.

FIG. 15 is a schematic diagram showing Application Example 4 of the two-dimensional gas analyzer apparatus 10C in FIG. 11 to semiconductor process processing, and FIG. 16 is a flowchart showing Application Example 4.

Referring to FIGS. 15 and 16, the semiconductor process processing includes, for example, a wafer manufacturing step (S1), a pre-step (S2), and a post-step (S3). In the wafer manufacturing step (S1), a semiconductor wafer is manufactured, and in the pre-step (S2), the wafer is mounted on a mounting table in a chamber, and a predetermined semiconductor film is formed on the wafer using a film forming apparatus. Further, in the post-step (S3), the wafer is cut to assemble individual semiconductor chips.

In the semiconductor process processing described above, particularly in the pre-step (S2), if there is moisture in the chamber, a highly pure semiconductor cannot be formed, and thus moisture detection measurement is required in order to secure this. By removing moisture while measuring moisture using the gas analyzer apparatus 10 to 10C according to the first to fourth embodiments, it is possible to realize a chamber environment substantially free of moisture.

Application Example 5

Figure 17:
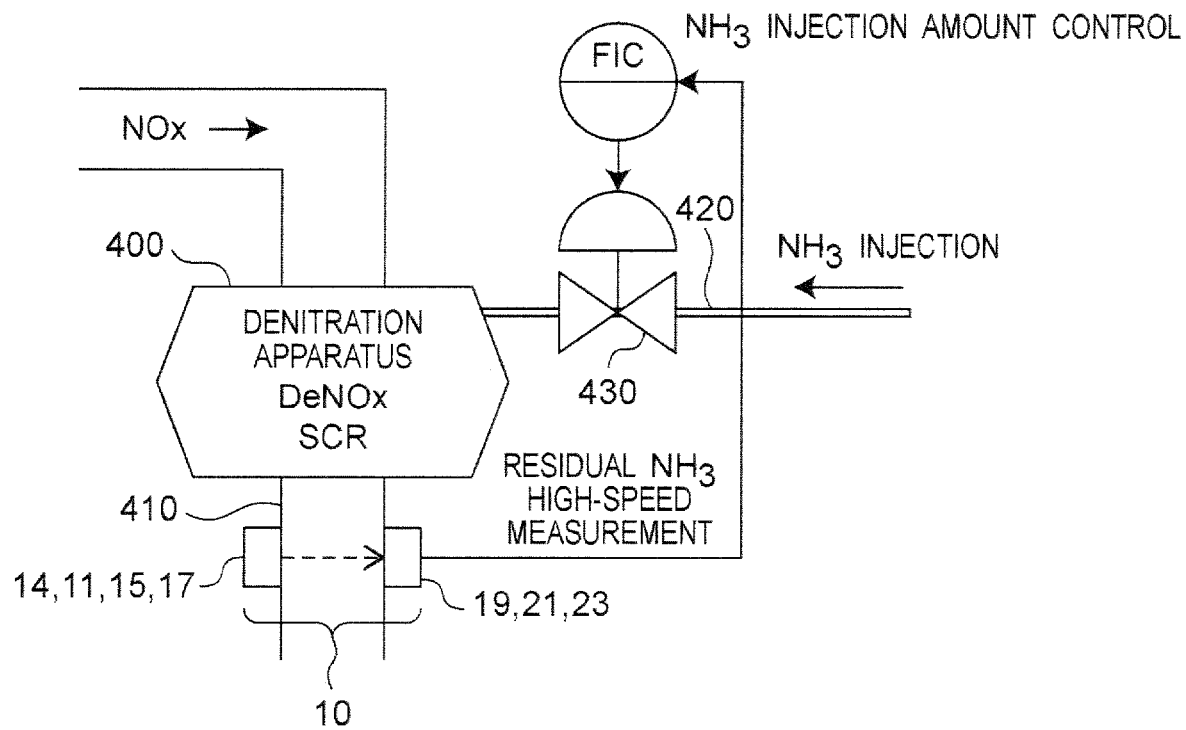
FIG. 17 is a schematic diagram showing Application Example 5 of the two-dimensional gas analyzer apparatus 10C in FIG. 11 to a denitration apparatus 400.

FIG. 17 is a schematic diagram showing Application Example 5 of the two-dimensional gas analyzer apparatus 10C in FIG. 11 to a denitration apparatus 400.

Referring to FIG. 17, the denitration apparatus 400 is, for example, an apparatus that denitrifies a gas such as NOx, and is configured such that the gas analyzer apparatus 10 is provided in an exhaust pipe 410, and the $NH_3$ injection amount in an injection valve 430 in an injection pipe 420 of $NH_3$ is controlled based on the measurement value of $NH_3$.

In the $NH_3$ measurement meter of an indirect $NO_x$ system represented by a chemiluminescence method, a zwitterion electrode method, or the like according to the conventional technology, there is such a problem that a maintenance load due to installation of a sample line by a heating conduit or a complicated measurement system is large in order to prevent $NH_3$ adsorption, and responsiveness is slow.

On the other hand, in the $NH_3$ measurement in FIG. 17, since the measurement is performed by directly installing the apparatus in the exhaust pipe 410 which is a process line, responsiveness and maintainability can be greatly improved as compared with the conventional technology. Furthermore, it is also possible to realize optimization of $NH_3$ injection by utilizing a measurement signal of the $NH_3$ concentration with good responsiveness for $NH_3$ injection amount control.

Application Example 6

Figure 18:
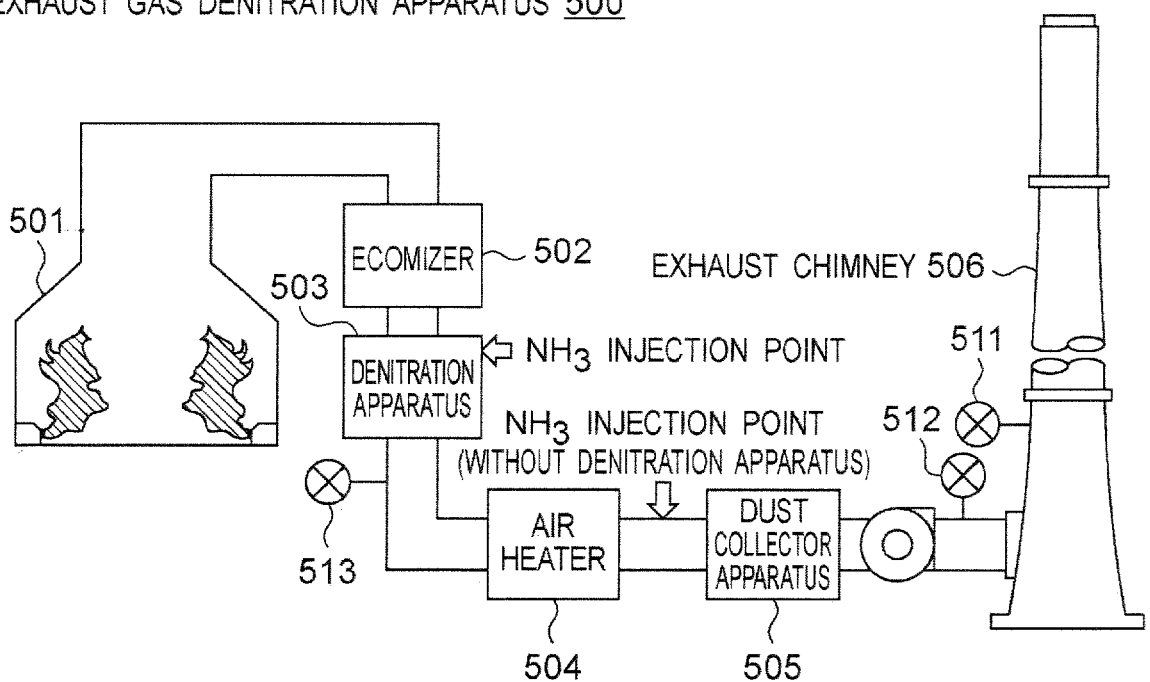
FIG. 18 is a flowchart showing Application Example 6 of the two-dimensional gas analyzer apparatus 10C in FIG. 11 to an exhaust gas denitration system 500.

FIG. 18 is a flowchart showing Application Example 6 of the two-dimensional gas analyzer apparatus 10C in FIG. 11 to an exhaust gas denitration system 500.

Referring to FIG. 18, the exhaust gas denitration system 500 includes a boiler 501, an economizer 502, a denitration apparatus 503, an air heater 504, a dust collector apparatus 505, and an exhaust chimney 506. The denitration apparatus 503 is provided for the purpose of improving a dust collection rate of a dust collection facility and preventing corrosion. In FIG. 17, the injection point of $NH_3$ is basically the denitration apparatus 503, but when the denitration apparatus 503 is not provided, as shown in FIG. 18, the injection point is provided between the air heater 504 and the dust collector apparatus 505. In this case, the two-dimensional gas analyzer apparatus 10C is provided, for example, in 511, 512 and 513.

In Application Example 6 configured as described above, it is possible to measure $NH_3$ with high accuracy and denitrate the exhaust gas. In particular, by using the two-dimensional gas analyzer apparatus 10C, high component selectivity, high-speed responsiveness, and improvement in maintainability can be obtained as compared with the conventional technology.

Application Example 7

For example, in a thermal power plant, the following configuration can be achieved by using the gas analyzer apparatus 10 to 10C according to the embodiments.

(1) In the boiler, by performing gas analysis control using the gas analyzer apparatus 10 to 10C, $NO_x$, CO, excessive $O_2$ can be reduced, and this leads to that combustion efficiency can be greatly improved as compared with the conventional technology.

(2) In the gas treatment apparatus in which discharge is performed from the boiler, the denitration efficiency can be improved, the ammonia slip can be reduced, and the life of the denitration catalyst can be lengthened as compared with the conventional technology.

Summary of Application Examples

As described above, according to the application examples using the gas analyzer apparatus 10 to 10C according to the embodiments, high component selectivity, high component selectivity, high-speed responsiveness, and improvement in maintainability can be obtained as compared with the conventional technology. In this case, not only $NH_3$ measurement but also measurement of CO and $O_2$ in optimum combustion control, measurement of trace moisture in an electrolytic plant or a semiconductor process, and the like are widely used for various industrial processes, and not only simple monitoring but also process control can greatly contribute to environmental conservation and running cost reduction.

Additional Implementation Examples

Implementation Example 1

Figure 19:
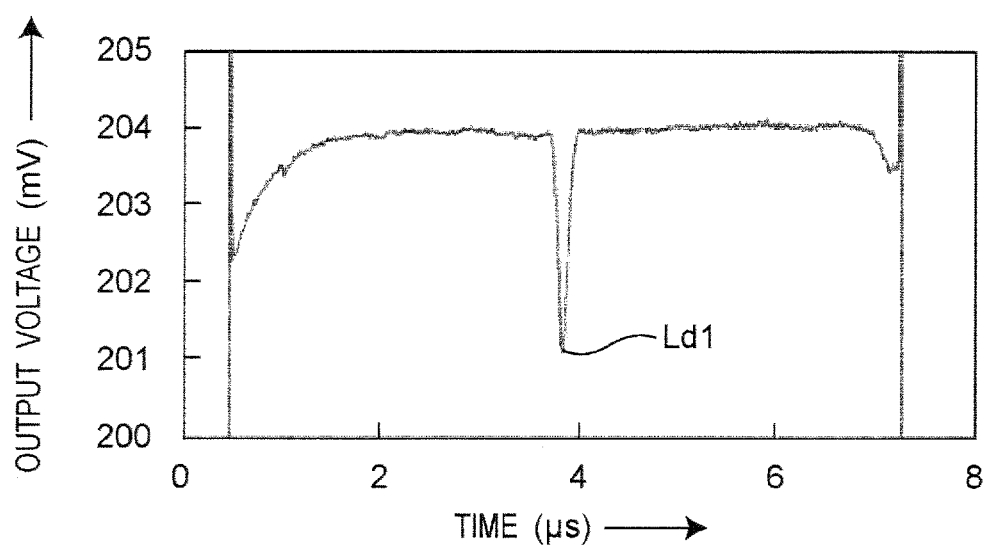
FIG. 19 is an experimental result of Implementation Example 1 of the gas analyzer apparatus 10 according to the first embodiment, and is a waveform chart showing an output voltage of the photodetector unit 19 when the target gas is $H_2O$ and the chamber pressure is 10 Torr (1.3 kPa).

FIG. 19 is an experimental result of Implementation Example 1 of the gas analyzer apparatus 10 according to the first embodiment, and is a waveform chart showing an output voltage of the photodetector unit 19 when the target gas is $H_2O$ and the chamber pressure is 10 Torr (1.3 kPa). In this case, specification conditions in the applicability test according to Implementation Example 1 are shown below.

Water vapor concentration: 0.7% (absolute concentration)
Laser path length: 100 mm
Modulation frequency: 50 kHz
Number of integrations: 654 times (13 ms)
Laser wavelength: 1392.5 nm
Pressure: 10 Torr (1.3 kPa)
Atmospheric pressure equivalent concentration: 92 ppm According to the test result of Implementation Example 1 in FIG. 19, the signal-to-noise power ratio (S/N) is 129 dB, and the atmospheric pressure equivalent concentration of 1 ppb can be obtained. As is clear from FIG. 19, the laser light can be generated such that each flat portion has a drop portion Ld1.

Implementation Example 2

Figure 20:
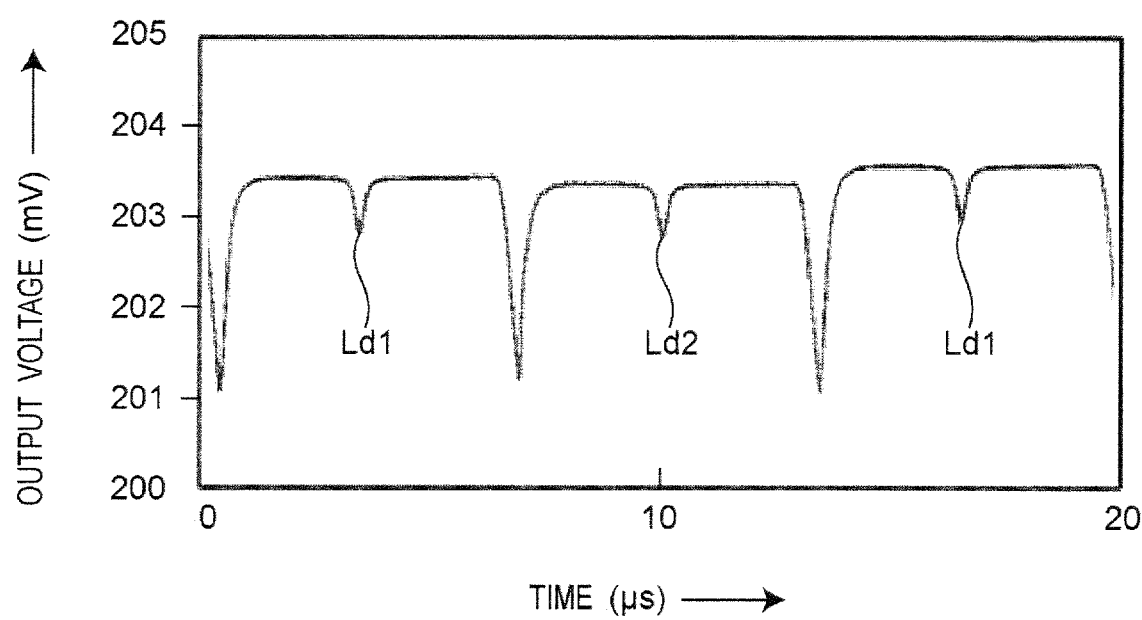
FIG. 20 is an experimental result of Implementation Example 2 of the gas analyzer apparatus 10A according to the second embodiment, and is a waveform chart showing an output voltage of the photodetector unit 19 when the target gas is $H_2O$ and the chamber pressure is 10 Torr (1.3 kPa).

FIG. 20 is an experimental result of Implementation Example 2 of the gas analyzer apparatus 10A according to the second embodiment, and is a waveform chart showing an output voltage of the photodetector unit 19 when the target gas is $H_2O$ and the chamber pressure is 10 Torr (1.3 kPa). In this case, specification conditions in the applicability test according to Implementation Example 2 are shown below.

Water vapor concentration: 0.7% (absolute concentration)
Laser path length: 100 mm
Modulation frequency: 50 kHz
Number of integrations: 654 times (13 ms)
Laser wavelength: 1392.5 nm
Pressure: 10 Torr (1.3 kPa)
Atmospheric pressure equivalent concentration: 92 ppm According to the test result of Implementation Example 2 in FIG. 20, as is clear from FIG. 20, the laser light can be generated to have drop portions Ld1 and Ld2 at different flat portions, respectively.

Implementation Example 3

Figure 21:
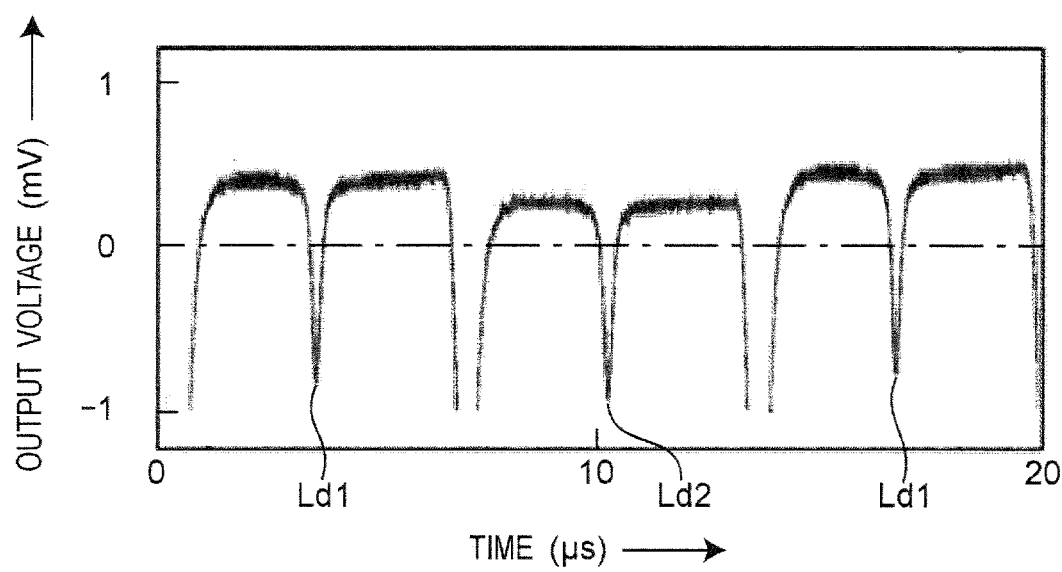
FIG. 21 is an experimental result of Implementation Example 2 of the gas analyzer apparatus 10A according to the second embodiment, and is a waveform chart showing an output voltage of the photodetector unit 19 showing that an amplification factor as an AC signal can be improved.

FIG. 21 is an experimental result of Implementation Example 2 of the gas analyzer apparatus 10A according to the second embodiment, and is a waveform chart showing an output voltage of the photodetector unit 19 showing that an amplification factor as an AC signal can be improved.

In the conventional example, in a case where the measurement is performed using the laser light having the laser intensity of the sawtooth wave, when the amplification factor as the AC signal is increased, a saturated state occurs in the upper part and the lower part of the AC signal, the generation of the laser light becomes unstable, and there is such a problem that there is an upper limit of the amplification factor for the stable operation. On the other hand, in the test result of the second embodiment, the amplification factor as the AC signal can be greatly improved by generating the laser light to have the drop portion in each flat portion. In particular, the amplification degree of the voltage signal can be greatly increased in the flat portion. Therefore, the sensitivity can be increased by about 100 times as the gas analysis capability.

INDUSTRIAL APPLICABILITY

As described above in detail, according to the present invention, the laser controller controls the laser light source such that the intensity of the laser light changes in a rectangular shape or a trapezoidal shape having at least a substantially flat amplitude in a predetermined time interval, and the wavelength of the laser light changes in the time interval. As a result, the detection accuracy of the gas analysis can be improved as compared with the conventional technology.

In addition, according to the application examples using the gas analyzer apparatus according to the present invention, high component selectivity, high-speed responsiveness, and improvement in maintainability can be obtained as compared with the conventional technology. In particular, in the semiconductor process, by using the gas analyzer apparatus of the present invention, moisture in a chamber in which a predetermined film is formed on a semiconductor wafer can be detected with higher accuracy than that in the conventional technology, which contributes to moisture removal, so that an extremely high effect is exhibited in industry.

Furthermore, the following industrial use is conceivable using the gas analyzer apparatus according to the present invention.

(1) In the automobile industry, exhaust gas management and combustion control can be performed. In particular, it can be used as an exhaust gas measuring apparatus for a new engine development tool of an automobile manufacturer.

(2) Step process management and control can be performed in various industrial apparatuses.

(3) Process monitoring and control in various plants can be performed. For example, it can be utilized for quality management and control in production processes such as synthetic chemical plants and steel plants, and specific components contained in gases such as raw materials and products can be monitored.

The invention claimed is:

1. A gas analyzer apparatus comprising:
a laser light source configured to irradiate measurement target gas with laser light;
a laser controller configured to control the laser light source to change a wavelength of the laser light in a predetermined wavelength band;
a photodetector unit configured to photoelectrically convert laser light having passed through the measurement target gas into an electric signal, and output the electric signal; and
an analyzer configured to analyze an absorption wavelength of the measurement target gas based on the electric signal,
wherein the laser controller comprises:
a signal generator configured to generate a voltage signal of a rectangular wave or a trapezoidal wave; and
a current power supply configured to convert the voltage signal into a drive current of a rectangular wave or a trapezoidal wave, and causes the drive current to flow through the laser light source, and
wherein the laser controller controls the laser light source such that an intensity of the laser light changes in a shape having a flat portion that is at least substantially constant in a predetermined time interval only by current control using the signal generator and the current power supply, and then, an output of the laser light changes, the temperature of the laser light source changes, and a spacing between diffraction gratings of the laser light source changes, thereby changing a wavelength of the laser light in the time interval so as to be substantially proportional to passed time according to rise of the temperature of the laser light source with a delay from a rise of the intensity of the laser light.

2. The gas analyzer apparatus as claimed in claim 1, wherein the shape is a rectangular shape or a trapezoidal shape.

3. The gas analyzer apparatus as claimed in claim 1, wherein the laser controller controls each of the laser light sources such that a variation of the flat portion is equal to or less than a predetermined threshold value.

4. The gas analyzer apparatus as claimed in claim 1, further comprising an amplifier that is provided between the photodetector and the analyzer, the amplifier being configured to amplify the electric signal.

5. A gas analyzer apparatus comprising:
a plurality of laser light sources that output a plurality of beams of laser light, respectively;
a laser controller configured to control each of the plurality of laser light sources to change a wavelength of each of the plurality of laser light beams in a predetermined wavelength band;

a multiplexer configured to multiplex the plurality of beams of laser light and irradiate measurement target gas with multiplexed light after multiplexing;
a photodetector unit configured to photoelectrically convert laser light having passed through the measurement target gas into an electric signal, and output the electric signal; and
an analyzer configured to analyze an absorption wavelength of the measurement target gas based on the electric signal,
wherein the laser controller comprises:
a signal generator configured to generate a voltage signal of a rectangular wave or a trapezoidal wave; and
a current power supply configured to convert the voltage signal into a drive current of a rectangular wave or a trapezoidal wave, and causes the drive current to flow through the plurality of laser light sources, and
wherein the laser controller controls the plurality of laser light sources such that the plurality of laser light sources sequentially and repeatedly output the plurality of beams of laser light so as not to overlap each other, and an intensity of each of the laser lights changes in a shape having a flat portion that is at least substantially constant in a predetermined time interval only by current control using the signal generator and the current power supply, and then, an output of each of the laser lights changes, the temperature of each of the laser light sources changes, and a spacing between diffraction gratings of each of the laser light sources changes, thereby changing a wavelength of each of the laser lights in the time interval so as to be substantially proportional to passed time according to rise of the temperature of each of the laser light sources with a delay from a rise of the intensity of each of the laser light.

6. The gas analyzer apparatus as claimed in claim 5,
wherein the shape is a rectangular shape or a trapezoidal shape.

7. The gas analyzer apparatus as claimed in claim 5,
wherein light intensities of the plurality of beams of laser light are substantially identical to each other, and each of the light intensities has a difference therebetween, which is equal to or less than a predetermined threshold value.

8. The gas analyzer apparatus as claimed in claim 5,
wherein the plurality of laser light sources include a first laser light source and a second laser light source,
wherein the first laser light source outputs first laser light,
wherein the second laser light source outputs second laser light, and
wherein the laser controller controls the first and second laser light sources to alternately and repeatedly output the first laser light and the second laser light.

9. The gas analyzer apparatus as claimed in claim 8, further comprising a demultiplexer configured to split the multiplexed light into a plurality of optical paths and irradiate the measurement target gas with the multiplexed light,
wherein the photodetector unit includes a plurality of photodetectors provided to correspond to the plurality of optical paths, respectively, each of the plurality of photodetectors being configured to photoelectrically convert laser light having passed through the measurement target gas into an electric signal, and output the electric signal,
wherein the analyzer analyzes the measurement target gas based on a plurality of electric signals outputted from the photodetectors,
wherein the laser controller controls the first and second laser light sources to make an amplitude of the first laser light and an amplitude of the second laser light different from each other, and
wherein the analyzer cancels an influence of a variation due to a factor other than original absorption in a waveform of each electric signal from each of the photodetectors based on a difference in amplitude between the first laser light and the second laser light.

10. The gas analyzer apparatus as claimed in claim 5,
wherein the laser controller controls the plurality of beams of laser light such that amplitudes of the plurality of beams of laser light are substantially identical to each other in the time interval, and the plurality of beams of laser light change in substantially identical wavelength band in the time interval.

11. The gas analyzer apparatus as claimed in claim 5,
wherein the laser controller controls the plurality of beams of laser light such that amplitudes of the plurality of beams of laser light are different from each other in the time interval and the plurality of beams of laser light change in wavelength bands substantially different from each other in the time interval.

12. A gas analysis method comprising the steps of:
irradiating, by a laser light source, measurement target gas with laser light;
controlling the laser light source to change a wavelength of the laser light in a predetermined wavelength band;
photoelectrically converting laser light having passed through the measurement target gas into an electric signal, and output the electric signal; and
analyzing an absorption wavelength of the measurement target gas based on the electric signal,
wherein the gas analysis method comprises the steps of:
generating, by a signal generator, a voltage signal of a rectangular wave or a trapezoidal wave; and
converting, by a current power supply, the voltage signal into a drive current of a rectangular wave or a trapezoidal wave, and causing the drive current to flow through the laser light source, and
wherein the step of controlling the laser light source includes controlling the laser light source such that an intensity of the laser light changes in a shape having a flat portion that is at least substantially constant in a predetermined time interval only by current control using the signal generator and the current power supply, and then, an output of the laser light changes, the temperature of the laser light source changes, and a spacing between diffraction gratings of the laser light source changes, thereby changing a wavelength of the laser light in the time interval so as to be substantially proportional to passed time according to rise of the temperature of the laser light source with a delay from a rise of the intensity of the laser light.

13. The gas analysis method as claimed in claim 12,
wherein the shape is a rectangular shape or a trapezoidal shape.

14. A gas analysis method comprising the steps of:
outputting, by a plurality of laser light sources, a plurality of beams of laser light, respectively;
controlling each of the plurality of laser light sources to change a wavelength of each of the plurality of laser light beams in a predetermined wavelength band;
multiplexing the plurality of beams of laser light and irradiating measurement target gas with multiplexed light after multiplexing;

photoelectrically converting laser light having passed through the measurement target gas and outputting an electric signal; and
analyzing an absorption wavelength of the measurement target gas based on the electric signal,
wherein the gas analysis method comprises the steps of:
generating, by a signal generator, a voltage signal of a rectangular wave or a trapezoidal wave; and
converting, by a current power supply, the voltage signal into a drive current of a rectangular wave or a trapezoidal wave, and causing the drive current to flow through the plurality of laser light sources, and
wherein the step of controlling the plurality of laser light sources comprises controlling the laser light sources such that the plurality of laser light sources sequentially and repeatedly output the plurality of beams of laser light so as not to overlap each other, and an intensity of each of the laser lights changes in a shape having a flat portion that is at least substantially constant in a predetermined time interval only by current control using the signal generator and the current power supply, and then, an output of each of the laser lights changes, the temperature of each of the laser light sources changes, and a spacing between diffraction gratings of each of the laser light sources changes, thereby changing a wavelength of each of the laser lights in the time interval so as to be substantially proportional to passed time according to rise of the temperature of each of the laser light sources with a delay from a rise of the intensity of each of the laser light.

15. The gas analysis method as claimed in claim 14, wherein the shape is a rectangular shape or a trapezoidal shape.

16. The gas analysis method as claimed in claim 14, wherein light intensities of the plurality of beams of laser light are substantially identical to each other, and each of the light intensities has a difference therebetween which is equal to or less than a predetermined threshold value.

\* \* \* \* \*